United States Patent [19]

Sasse et al.

[11] 4,067,726
[45] Jan. 10, 1978

[54] 3-UREIDO PHENYLACETAMIDE HERBICIDES

[75] Inventors: Klaus Sasse, Schildgen; Ludwig Eue, Cologne, both of Germany

[73] Assignee: Bayer Aktiengesellschaft, Leverkusen, Germany

[21] Appl. No.: 573,205

[22] Filed: Apr. 30, 1975

[30] Foreign Application Priority Data

May 15, 1974 Germany ............................. 2423536

[51] Int. Cl.² .......................... A01N 9/12; A01N 9/20; C07C 157/09; C07C 127/19
[52] U.S. Cl. ................................... 71/120; 544/133; 544/152; 544/145; 544/114; 544/130; 544/131; 544/135; 544/139; 544/141; 544/140; 544/132; 260/239.8; 260/243.3; 260/250 B; 260/250 A; 260/256.4 R; 260/268 C; 260/294.8 H; 260/294.9; 260/293.73; 260/293.75; 260/293.79; 260/293.81; 260/295 E; 260/302 A; 260/302 R; 260/302 D; 260/307 R; 544/58; 544/86; 544/112; 544/113
[58] Field of Search .......... 260/465 D, 471 R, 552 R, 260/553 A, 454; 71/99, 105, 111, 120, 103, 104

[56] References Cited
U.S. PATENT DOCUMENTS

| 3,532,738 | 10/1970 | Wilson et al. ............. 260/553 A X |
| 3,646,136 | 2/1972 | Hoegerle et al. ............. 260/553 A |
| 3,806,537 | 4/1974 | Dorschner et al. ................. 71/99 X |
| 3,867,426 | 2/1975 | Olin et al. .................... 260/553 A X |
| 3,897,493 | 7/1975 | Teach ............................. 260/553 A |

OTHER PUBLICATIONS

Jacobs et al., J.A.C.S. 39, p. 2438.

Primary Examiner—Daniel E. Wyman
Assistant Examiner—Thomas A. Waltz
Attorney, Agent, or Firm—Burgess, Dinklage & Sprung

[57] ABSTRACT

New 3-amino-phenylacetic acid compounds of the formula:

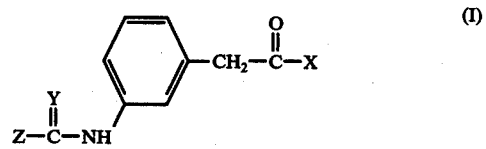

wherein
X is hydrocarbyloxy or hydrocarbylthio optionally substituted by halogen, alkoxy, aryloxy, alkylmercapto or arylmercapto, or X is mono- or disubstituted amino, or represent a 5- to 8-membered heterocyclic ring;
Y is oxygen or sulfur;
Z is optionally substituted hydrocarbyl or hydrocarbyloxy or -thio, or Z can represent mono- or disubstituted amino, or a closed heterocyclic ring;

possess outstanding herbicidal activity, both pre-emergence and post-emergence.

22 Claims, No Drawings

3-UREIDO PHENYLACETAMIDE HERBICIDES

The present invention relates to new 3-amino-phenylacetic acid compounds, to herbicidal compositions containing them, and to their use as herbicides.

It is known that 3-ureido-phenylacetic acid amide can be synthesized by the action of cyanic acid on 3-amino-phenylacetic acid amide (Compare J. Amer. Chem. Soc. 39, 2438 (1917)). As also known in the literature, the reaction of 3-amino-phenylacetic acid with acetic anhydride gives 3-acetylamino-phenylacetic acid (Compare J. Biol. Chem. 68, 507 (1926)). However, these previously disclosed compounds are not known to have herbicidal properties.

Further, it has already been disclosed that certain carbamic acid esters which contain two urethane groupings can be used as herbicides. Thus, for example, 3-methoxycarbonylaminophenyl-N-(3'-methylphenyl)-carbamate can be employed for combating weeds (Compare German Offenlegungeschrift (German Published Specification) 1,567,151). However, the activity of this compound is not always entirely satisfactory, especially if low amounts and low concentrations are used.

The present invention provides certain 3-amino-phenylacetic acid compounds which overcome these disadvantages to a substantial extent. Surprisingly, the 3-amino-phenylacetic acid derivatives according to the invention, of the formula (I), exhibit a substantially better herbicidal activity, both in preemergence and in post-emergence use, than 3-methoxycarbonylaminophenyl-N-3'-methyl-phenyl)-carbamate, known in the art, which is the nearest active compound of the same type of action. The compounds according to the invention thus represent a valuable enrichment of the art.

The 3-amino-phenylacetic acid derivatives provided by the present invention of the formula

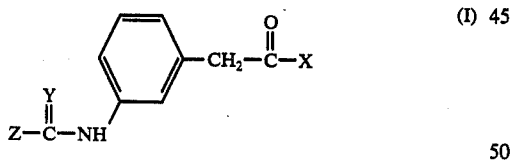

in which X represents the group OR or SR in which
R is alkyl of from 1 to 6 carbon atoms optionally substituted by halogen, alkoxy, aryloxy, alkylmercapto or arylmercapto, or R is alkenyl of from 3 to 6 carbon atoms optionally substituted by halogen, alkoxy, arloxy, alkylmercapto or arylmercapto, or R is alkynyl of from 3 to 6 carbon atoms optionally substituted by halogen, alkoxy, aryloxy, alkylmercapto or arylmercapto, or R is optionally alkyl-substituted cycloalkyl of from 4 to 6 carbon atoms in the cycloalkyl radical, or R is aralkyl of from 1 to 4 carbon atoms in the alkyl moiety and 6 and 10 carbon atoms in the aryl moiety, the aryl moiety optionally being substituted by halogen, alkyl, haloalkyl, alkoxy, alkylmercapto and/or nitro, or X represents the group

in which
R¹ is hydrogen, alkyl of from 1 to 4 carbon atoms or alkenyl of from 2 to 4 carbon atoms, and
R² is alkyl of from 1 to 15 carbon atoms, alkenyl of from 3 to 12 carbon atoms or alkynyl of from 3 to 12 carbon atoms, each of these alkyl, alkenyl and alkynyl radicals being optionally substituted by halogen, cyano, carboxylic acid ester groups, carboxylic acid amide groups, alkoxy, aryloxy, alkylmercapto, arylmercapto, alkylsulphonyl or arylsulphonyl, or by aryl optionally substituted by halogen, alkyl, haloalkyl, alkoxy, alkylmercapto and/or nitro, or by optionally substituted cycloalkyl of from 3 to 6 carbon atoms and/or by 5-membered or 6-membered heterocyclic groups of from 1 to 3 hetero-atoms in the ring, or R² is cycloalkyl of from 3 to 8 carbon atoms in the ring, optionally substituted by alkyl, halogen or alkoxy, or R² is aryl of from 6 to 10 carbon atoms, optionally monosubstituted or polysubstituted by halogen, nitro, cyano, carboxylic acid ester or carboxylic acid amide, alkyl of from 1 to 6 carbon atoms, cycloalkyl of from 5 or 6 carbon atoms, alkoxy, haloalkoxy, aryloxy, alkylmercapto, arylmercapto, alkylsulphonyl, arylsulphonyl, haloalkyl and/or thiocyano, or R² is a 5-membered or 6-membered heterocyclic radical of from 1 to 3 hetero-atoms in the ring, with further rings optionally being fused to the heterocyclic ring, or R¹ and R² together with the adjoining nitrogen atom form an optionally substituted 5-membered to 8-membered heterocyclic ring in which 1 to 3 carbon atoms can be replaced by oxygen, nitrogen, sulphur, SO₂ or N-alkyl, and which can be fused to other carbocyclic or heterocyclic ring systems,
y is oxygen or sulphur, and
Z is alkyl of from 1 to 12 carbon atoms, alkenyl of from 2 to 12 carbon atoms or alkynyl of from 2 to 6 carbon atoms, each of these alkyl, alkenyl and alkynyl radicals being optionally monosubstituted or polysubstituted by halogen, alkoxy, optionally substituted aryloxy, alkylmercapto, optionally substituted arylmercapto or optionally halogen-substituted or alkylsubstituted aryl of from 6 to 10 carbon atoms, or Z is cycloalkyl of from 3 to 6 carbon atoms and/or is aryl optionally monosubstituted or polysubstituted by halogen, alkyl, haloalkyl, nitro and/or alkoxy, or Z represents the group OR³ or SR³, in which
R³ is alkyl of from 1 to 6 carbon atoms or alkenyl of from 2 to 6 carbon atoms, each of these alkyl or alkenyl radicals being optionally substituted by halogen, alkoxy, optionally substituted aryloxy and/or aryl which is optionally substituted by halogen, nitro, alkyl and/or alkoxy, or R³ is optionally substituted alkynyl of from 3 to 6 carbon atoms, or
Z represents the group

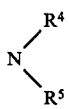

in which
- R[4] is hydrogen, alkyl of from 1 to 4 carbon atoms or alkenyl of from 2 to 4 carbon atoms, and
- R[5] is alkyl of from 1 to 4 carbon atoms which is optionally substituted by halogen or alkoxy, alkenyl of from 2 to 4 carbon atoms, alkynyl of from 3 to 6 carbon atoms or optionally alkylsubstituted cycloalkyl of 5 or 6 carbon atoms, or
- R[4] and R[5] together with the adjoining nitrogen atom form an optionally substituted 5-membered to 8-membered heterocyclic ring in which 1 to 3 carbon atoms can be replaced by oxygen, nitrogen, sulphur, SO$_2$ or N-alkyl.

The hetero-atoms mentioned in the definition of R[2] may for example be sulphur, oxygen or nitrogen atoms.

When R is straight-chain or branched alkyl of from 1 to 6 carbon atoms, it preferably has 1 to 4 carbon atoms, and such alkyl can carry one or more identical or different preferred substituents from amongst the following: fluorine, chlorine, bromine, iodine, alkoxy of from 1 to 4 carbon atoms (especially 1 or 2 carbon atoms), aryloxy with 6 to 10 carbon atoms (for example phenoxy), alkylmercapto with 1 to 4 carbon atoms (especially 1 or 2 carbon atoms), and arylmercapto of from 6 to 10 carbon atoms, especially phenylmercapto.

When R is straight-chain or branched alkenyl or alkynyl of from 3 to 6 carbon atoms, and such alkenyl and alkynyl can carry one or more identical or different preferred substituents from amongst the following: fluorine, chloride, bromine, iodine, alkoxy of from 1 to 4 carbon atoms (especially 1 or 2 carbon atoms), aryloxy of from 6 to 10 carbon atoms (for example phenoxy), alkylmercapto of from 1 to 4 carbon atoms (expecially 1 or 2 carbon atoms), and arylmercapto of from 6 to 10 carbon atoms (especially phenylmercapto).

When R is cyclopentyl or cyclohexyl, such radicals can carry one or more identical or different alkyl substituents of from 1 to 4 carbon atoms, preferably of 1 or 2 carbon atoms, especially methyl.

When R is aralkyl it preferably has 1 or 2 carbon atoms in the alkyl moiety. Examples of aryl moieties are phenyl and naphthyl. Benzyl and 2-phenylethyl may be mentioned especially as aralkyl radicals. Such aralkyl radicals can be substituted in the aryl moiety by one or more identical or different radicals from amongst the following: fluorine, chlorine, bromine, iodine, alkyl of from 1 to 4 carbon atoms (especially methyl and ethyl), haloalkyl of from 1 to 4 carbon atoms and 1 to 5 halogen atoms, (especially trifluoromethyl), alkoxy of from 1 to 4 carbon atoms (especially 1 or 2 carbon atoms), alkylmercapto of from 1 to 4 carbon atoms (especially 1 or 2 carbon atoms), and nitro.

R[1] is preferably hydrogen, straight-chain or branched alkyl of from 1 to 3 carbon atoms or straight-chain or branched alkenyl of from 2 to 4 carbon atoms.

When R[2] is alkyl it is preferably straight-chain or branched alkyl of from 1 to 12 carbon atoms, and when it is alkenyl or alkynyl of from 3 to 6 carbon atoms, and such alkyl, alkenyl and alkynyl radicals can carry one or more identical or different preferred substituents from amongst the following: fluorine, chlorine, bromine, iodine, cyano, carbalkoxy of from 1 to 4 carbon atoms in the alkyl moiety, alkylaminocarbonyl or dialkylaminocarbonyl of from 1 to 4 carbon atoms in each alkyl moiety, alkoxy of from 1 to 4 carbon atoms (especially 1 or 2 carbon atoms), aryloxy of from 6 to 10 carbon atoms (especially phenoxy), alkylmercapto of from 1 to 4 carbon atoms (especially 1 or 2 carbon atoms), arylmercapto of from 6 to 10 carbon atoms (especially phenylthio), alkylsulphonyl with 1 to 4 carbon atoms (especially 1 or 2 carbon atoms), arylsulphonyl of from 6 to 10 carbon atoms (preferably phenylsulphonyl), aryl with 6 to 10 carbon atoms (especially phenyl or naphthyl), such aryl being optionally monosubstituted or polysubstituted by identical or different substituents (preferably by halogen, especially fluorine, chlorine, bromine or iodine), alkyl of from 1 to 3 carbon atoms, haloalkyl of from 1 to 3 carbon atoms and 1 to 5 halogen atoms, alkoxy of from 1 to 3 carbon atoms, alkylmercapto of from 1 to 3 carbon atoms and/or nitro, cycloalkyl of 5 or 6 carbon atoms in the ring, such cycloalkyl optionally being substituted by alkyl of from 1 to 3 carbon atoms, and 5-membered or 6-membered heterocyclic radicals of from 1 to 3 hetero-atoms (such as oxygen, sulphur and nitrogen) in the ring, examples which may be mentioned of heterocyclic radicals being pyrrolidinyl, piperidinyl, furyl, thiophenyl, pyazolyl, imidazolyl, 1,2,3-triazolyl, 1,2,4-triazolyl, benztriazolyl, oxazolyl, isoxazolyl, 1,3-thiazolyl, isothiazolyl, benthiazolyl, pyrrolyl, pyridyl, piperazinyl, pyridazinyl, pyrimidinyl, pyrazinyl, 1,3,5-, 1,2,4- and 1,2,3-triazinyl.

When R[2] is cycloalkyl it preferably has 3 to 6 carbon atoms, and such cycloalkyl can carry one or more identical or different substituents from amongst the following: alkyl of from 1 to 3 carbon atoms (for example methyl), fluorine, chlorine, bromine, iodine, and alkoxy of from 1 to 3 carbon atoms.

When R[2] is aryl it may be phenyl or naphthyl. Such aryl can carry one or more identical or different substituents from amongst the following: fluorine, chlorine, bromine, iodine, nitro, cyano, thiocyano, carbalkoxy of from 1 to 4 carbon atoms in the alkyl moiety, alkylaminocarbonyl or dialkylaminocarbonyl of from 1 to 4 carbon atoms in each alkyl moiety, alkyl of from 1 to 4 carbon atoms (especially 1 or 2 carbon atoms), cyclohexyl, cyclopentyl, alkoxy of from 1 to 4 carbon atoms (especially 1 or 2 carbon atoms), haloalkoxy of from 1 to 4 carbon atoms and 1 to 5 halogen atoms (for example trifluoromethoxy), aryloxy of from 6 to 10 carbon atoms (especially phenoxy), alkylmercapto of from 1 to 4 carbon atoms (especially 1 or 2 carbon atoms), arylmercapto of from 6 to 10 carbon atoms (especially phenylthio), alkylsulphonyl of from 1 to 4 carbon atoms (especially 1 or 2 carbon atoms) and arylsulphonyl of from 6 to 10 carbon atoms (for example phenylsulphonyl), and haloalkyl of from 1 to 4 carbon atoms and 1 to 5 halogen atoms (especially trifluoromethyl).

When R[2] is a heterocyclic radical it may for example be furyl, thiophenyl, pyrazolyl, imidazolyl, 1,2,3-triazolyl, 1,2,4-triazolyl, oxazolyl, isoxazolyl, 1,3-triazolyl, isothiazolyl, benzthiazolyl, pyrrolyl, pyridyl, piperazinyl, pyridazinyl, pyrimidinyl, pyrazinyl or 1,3,5-, 1,2,4- or 1,2,3-triazinyl.

When R[1] and R[2] together with the adjoining nitrogen atom for a heterocyclic ring, the ring may be a saturated or unsaturated ring with 5 or 6 ring members, and such ring can contain, as further hetero-atoms (in addition to the said nitrogen), 1 to 3 (preferably 1) oxygen, sulphur or nitrogen atoms, and, as hetero-groups, preferably an SO₂ or N-alkyl group, wherein the alkyl of the N-alkyl group preferably contains 1 to 4, (especially 1 or 2) carbon atoms. Each of such heterocyclic rings can be substituted, for example by halogen and/or alkyl of from 1 to 4 carbon atoms, and can furthermore be fused to other carbocyclic or heterocyclic ring systems with 5 or 6 ring members. Pyrrolidinyl, piperidinyl, piperazinyl, hexamethyleneimidinyl, morpholinyl, thiamorpholinyl, sulphamorpholinyl, N-methylpiperazinyl, 1,2,4-triazinyl, imidazolyl and benztriazolyl may be mentioned as examples of the heterocyclic radicals.

When Z is alkyl it may of course be straight-chain or branched alkyl, and it preferably has 1 to 6 carbon atoms; when Z is alkenyl it may of course be straight-chain or branched alkenyl, and it preferably has 2 to 6 carbon atoms (especially 2 to 4 carbon atoms); and when Z is alkynyl it preferably has 2 to 4 carbon atoms. Each of such alkyl, alkenyl and alkynyl radicals can carry one or more identical or different substituents from amongst the following: fluorine, chlorine, bromine, iodine, aryl with 6 or 10 carbon atoms (for example phenyl and naphthyl) optionally substituted by alkyl of from 1 to 3 carbon atoms and/or by halogen (especially fluorine or chlorine), alkoxy of from 1 to 4 carbon atoms (especially 1 or 2 carbon atoms) aryloxy of 6 or 10 carbon atoms (especially phenoxy) optionally substituted by alkyl of from 1 to 3 carbon atoms and/or by halogen (especially fluorine or chlorine), alkylmercapto of from 1 to 4 carbon atoms (especially 1 or 2 carbon atoms), and arylmercapto of 6 or 10 carbon atoms (for example phenylthio) optionally substituted by alkyl of from 1 to 3 carbon atoms and/or by halogen (especially fluorine or chlorine).

When Z is cycloalkyl it may for example by cyclopropyl, cyclopentyl or cyclohexyl.

When Z is aryl it preferably is aryl with 6 or 10 carbon atoms (especially phenyl or naphthyl) and such aryl radicals can carry one or more identical or different substituents from amongst the following: fluorine, chlorine, bromine, iodine, alkyl of from 1 to 4 carbon atoms (especially 1 or 2 carbon atoms), haloalkyl of from 1 to 4 carbon atoms and 1 to 5 halogen atoms, nitro, and alkoxy of from 1 to 4 carbon atoms (especially 1 or 2 carbon atoms).

When Z represents the group R³O— or R³S—, R³ preferably represents straight-chain or branched alkyl of from 1 to 4 carbon atoms, straight-chain or branched alkenyl of from 2 to 4 carbon atoms, or straight-chain or branched alkynyl of from 3 to 6 carbon atoms, and each of such alkyl, alkenyl and alkynyl radicals can carry one or more identical or different substituents from amongst the following: fluorine, chlorine, bromine, iodine, alkoxy of from 1 to 4 carbon atoms (especially 1 or 2 carbon atoms), aryloxy with 6 or 10 carbon atoms (especially phenoxy) optionally susbstituted by alkyl of from 1 to 3 carbon atoms and/or by halogen (especially fluorine or chlorine), and aryl with 6 or 10 carbon atoms (especially phenyl) optionally substituted by fluorine, chlorine, bromine, iodine, nitro, alkyl of from 1 to 3 carbon atoms and/or alkoxy of from 1 to 3 carbon atoms.

When Z represents the group

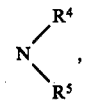

then: R⁴, when it is alkyl or alkenyl, is preferably straight-chain or branched alkyl of from 1 to 3 carbon atoms (especially methyl) or alkenyl of 3 carbon atoms; and R⁵, when it is alkyl, may of course be straight-chain or branched, and such alkyl can be monosubstituted or polysubstituted by identical or different substituents from amongst: fluorine, chlorine, bromine, iodine, and alkoxy of from 1 to 3 carbon atoms, or R⁵, when it is alkenyl or alkynyl, may of course by straight-chain or branched, or R⁵, when it is cycloalkyl, can be monosubstituted or polysubstituted by alkyl of from 1 to 3 carbon atoms (especially methyl); or R⁴ and R⁵, when they form, together with the adjoining nitrogen atom, a saturated or unsaturated heterocyclic ring, this preferably has 5 or 6 ring members, and the heterocyclic ring can contain as further hetero-atoms (in addition to the said nitrogen) 1 to 3 (preferably 1) oxygen, sulphur or nitrogen atoms and, as hetero-groups, SO₂ or N-alkyl groups, the alkyl of such N-alkyl group preferably containing 1 to 4 (especially 1 or 2) carbon atoms. The heterocyclic ring can be substituted by substituents such as halogen (especially fluorine or chlorine) and/or alkyl of from 1 to 4 carbon atoms. Pyrrolidnyl, piperidinyl, piperazinyl, hexamethyleneimidinyl, morpholinyl, thiamorpholinyl, sulfamorpholinyl, N-methylpiperazinyl, 1,2,4-triazolyl, imidazolyl and 3,5-dimethyl-morpholinyl may be mentioned as examples of the heterocyclic radicals.

The invention also provides a process for the production of a 3-amino-phenylacetic acid derivative of the formula (I) in which, as appropriate to give the desired product:

a. a compound of the formula

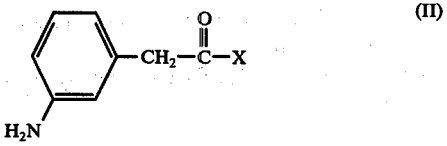

wherein
X has the above-mentioned meaning is reacted either
(α) with a compound of the formula

wherein
Y and Z have the above-mentioned meanings and
Q represents halogen or the group OR³ or O—CO—R³
wherein
R³ has the above-mentioned meaning, or
(β) with an isocyanate or isothiocyanate of the formula:

 (IV)

wherein
R⁵ and Y have the above-mentioned meanings, optionally in the presence of a diluent and optionally in the presence of an acid-binding agent,
or
b. a compound of the formula:

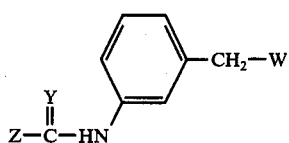 (V)

in which
Y and Z have the abovementioned meanings and
W represents CN or the group R⁶—CO—in which R⁶ is hydroxyl, halogen, alkoxy, haloalkoxy, or aryloxy which is optionally substituted by halogen, alkyl and/or nitro,
is reacted with an alcohol, mercaptan or amine of the formula
 (VI)

in which
X has the abovementioned meaning or with an alkali metal salt of such an alcohol or mercaptan optionally in the presence of a diluent and optionally in the presence of an acid-binging agent and optionally in the presence of a catalyst,
or
c. a 3-isocyanato- or 3-isothiocyanato-phenylacetic acid halide of the formula

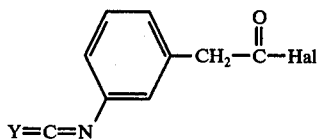 (VII)

in which
Y has the abovementioned meaning and
Hal is halogen
is reacted with an alcohol, mercaptan or amine of the formula

 (VI)

in which
X has the abovementioned meaning optionally in the presence of a diluent and optionally in the presence of an acid-binding agent,
or
d. a 3-isocyanato- or 3-isothiocyanato-phenylacetic acid derivative of the formula

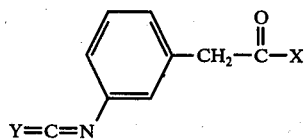 (VIII)

in which

X and Y have the abovementioned meanings is reacted with an alcohol or mercaptan of the formula

 (IX)

or

 (X)

in which
R³ has the abovementioned meaning or with an amine of the formula

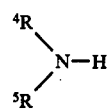 (XI)

in which
R⁴ and R⁵ have the abovementioned meanings, optionally in the presence of a diluent and optionally in the presence of a catalyst.

If 3-amino-phenylacetic acid anilide and propionic acid chloride are used as starting materials, the course of the reaction according to process variant (a) (subvariant (α)) can be represented by the following formula scheme:

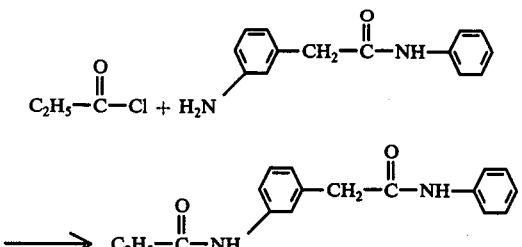

If 3-amino-phenylacetic acid anilide and methyl isocyanate are used as starting materials, the course of the reaction according to process variant (a) (subvariant (β)) can be represented by the following formula scheme:

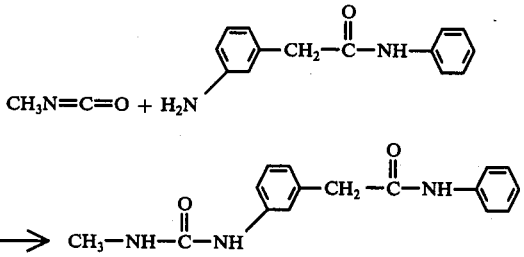

If 3-methoxycarbonylamino-phenylacetic acid and methanol are used as starting materials, the course of the reaction according to process variant (b) can be represented by the following formula scheme:

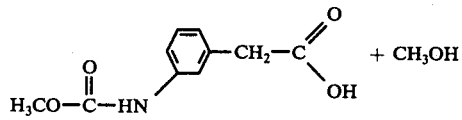

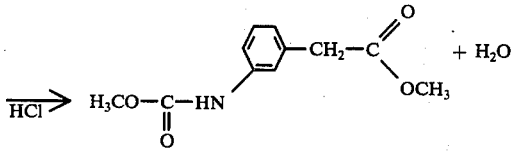

If 3-isocyanato-phenylacetic acid chloride and isopropanol are used as starting materials, the course of the reaction according to process variant (c) can be represented by the following formula scheme:

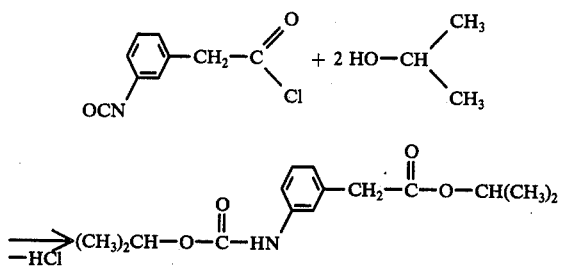

If 3-isocyanato-phenylacetic acid ethyl ester and dimethylamine are used as starting materials, the course of the reaction according to process variant (d) can be represented by the following formula scheme:

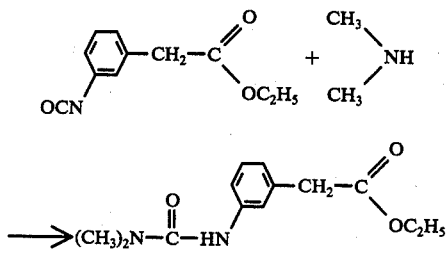

The compounds usable as starting materials in carrying out the process variants (a) – (d) according to the invention are generally defined by the formulae (II) to (XI).

The following may be mentioned as examples of the compounds of the formula (II): (3-amino-phenyl)-acetic acid methyl ester, (3-amino-phenyl)-acetic acid iso-propyl ester, (3-amino-phenyl)-acetic acid hexyl ester, (3-amino-phenyl)-acetic acid allyl ester, (3-amino-phenyl)-acetic acid propargyl ester, (3-amino-phenyl)-acetic acid 2-chloro-ethyl ester, (3-amino-phenyl)-acetic acid 2-ethoxy-ethyl ester, (3-aminophenyl)-acetic acid 2-phenoxy-ethyl ester, (3-amino-phenyl)-actic acid 2-ethylmercapto-ethyl ester, (3-amino-phenyl)-acetic acid 2-phenylmercapto-ethyl ester, (3-amino-phenyl)-acetic acid 4-chloro-butin-(2)-yl ester, (3-amino-phenyl)-acetic acid benzyl ester, (3-amino-phenyl)-acetic acid 2-phenyl-ethyl ester, (3-amino-phenyl)-acetic acid 4-chloro-benzyl ester, (3-amino-phenyl)-acetic acid 4-methyl-benzylester, (3-amino-phenyl)-acetic acid 4-trifluoromethyl-benzyl ester, (3-amino-phenyl)-acetic acid 4-methoxy-benzyl ester, (3-amino-phenyl)-acetic acid 4-methyl-mercapto-benzyl ester, (3-amino-phenyl)-acetic acid 3-nitro-benzyl ester, (3-aminophenyl)-acetic acid cyclopentyl ester, (3-amino-phenyl)acetic acid cyclohexyl ester,(3-amino-phenyl)-acetic acid 4-methyl-cyclohexyl ester, (3-amino-phenyl)-thioacetic acid S-methyl ester, (3-amino-phenyl)-thioacetic acid S-butyl ester, (3-amino-phenyl)-thioacetic acid S-allyl ester, (3-aminophenyl)-thioacetic acid S-benzyl ester, (3-amino-phenyl)-thioacetic acid S-4-chloro-benzyl ester, (3-amino-phenyl)-thioacetic acid S-cyclohexyl ester, (3-amino-phenyl)-acetic acid methylamide, (3-amino-phenyl)-acetic acid ethylamide, (3-amino-phenyl)-acetic acid isopropylamide, (3-amino-phenyl)-acetic acid butylamide, (3-amino-phenyl)-acetic acid sec.butylamide, (3-amino-phenyl)-acetic acid dodecylamide, (3-amino-phenyl)-acetic acid allylamide, (3-aminophenyl)-acetic acid 2-methyl-butin-(3)-yl-(2)-amide, (3-aminophenyl)acetic acid 2-chloro-ethyl amide, (3-amino-phenyl)-acetic acid 3-cyano-propyl amide, (3-amino-phenyl)-acetic acid carboethoxymethylamide, (3-amino-phenyl)-acetic acid dimethylcarbamido methylamide, (3-amino-phenyl)-acetic acid 3-ethoxy-propylamide, (3-amino-phenyl)-acetic acid 2-phenoxyethylamide, (3-amino-phenyl)-acetic acid 2-methyl mercaptoethyl-amide, (3-amino-phenyl)-acetic acid 2-phenylmercaptoethyl-amide, (3-amino-phenyl)-acetic acid 2-ethyl sulphonylethyl-amide, (3-amino-phenyl)-acetic acid 2-phenylsulphonylethyl-amide, (3-amino-phenyl)-acetic acid benzyl-amide, (3-amino-phenyl)-acetic acid 1-phenyl-ethyl-amide, (3-aminophenyl)-acetic acid 4-methyl-benzyl-amide, (3-amino-phenyl)-acetic acid 3,4-dichloro-benzyl-amide, (3-amino-phenyl)-acetic acid 4-trifluoromethyl-benzyl-amide, (3-amino-phenyl)-acetic acid 4-methoxy-benzyl-amide, (3-amino-phenyl)-acetic acid 4-methylmercapto-benzyl-amide, (3-amino-phenyl)-acetic acid 3-nitrobenzyl-amide, (3-amino-phenyl)-acetic acid α-naphthylmethylamide, (3-amino-phenyl)-acetic acid cyclohexylmethyl-amide, (3-amino-phenyl)-acetic acid cyclopropylamide, (3-aminophenyl)-acetic acid cyclopentyl amide, (3-amino-phenyl)-acetic acid cyclohexylamide, (3-amino-phenyl)-acetic acid 4-methylcyclohexyl-amide, (3-amino-phenyl)-acetic acid 4-chlorocyclohexyl-amide, (3-amino-phenyl)-acetic acid anilide, (3-amino-phenyl)-acetic acid 3-chloro-anilide, (3-aminophenyl)-acetic acid 4-chloro-anilide, (3-amino-phenyl)-acetic acid 3,4-dichloro-anilide, (3-amino-phenyl)-acetic acid 4-bromoanilide, (3-amino-phenyl)-acetic acid 4-iodo-anilide, (3-aminophenyl)-acetic acid 4-fluoro-anilide, (3-amino-phenyl)-acetic acid 4-nitro-anilide, (3-amino-phenyl)-acetic acid 4-cyanoanilide, (3-amino-phenyl)-acetic acid 4-carboethoxy-anilide, (3-amino-phenyl)-acetic acid 4-dimethylcarbamoyl-anilide, (3-amino-phenyl)-acetic acid 3-methyl-anilide, (3-aminophenyl)-acetic acid 3-chloro-4-methyl-anilide, (3-aminophenyl)-acetic acid 4-isopropyl-anilide, (3-amino-phenyl)-acetic acid 4-cyclohexyl-anilide, (3-amino-phenyl)-acetic acid 4-methoxy-anilide, (3-aminophenyl)-acetic acid 4-trifluoromethoxy-anilide, (3-amino-phenyl)-acetic acid 4-phenoxyanilide, (3-aminophenyl)-acetic acid 4-methylmercaptoanilide, (3-aminophenyl)-acetic acid 4-phenylmercaptoanilide, (3-aminophenyl)-acetic acid 4-methylsulphonylanilide, (3-aminophenyl)-acetic acid 4-phenylsulphonylanilide, (3-aminophenyl)-acetic acid 3-trifluoromethylanilide, (3-aminophenyl)-acetic acid 4-thiocyano-anilide, (3-aminophenyl)-acetic acid β-naphthylamide, (3-aminophenyl)-acetic acid furfurylamide, (3-amino-phenyl)-acetic acid thienylamide, (3-amino-phenyl)-acetic acid 1,3-thiazolylamide, (3-amino-phenyl)-acetic acid benzthiazolyl-(2)-amide, (3-amino-phenyl)-acetic acid 1,2,4-triazolyl-(3)-amide, (3-amino-phenyl)-acetic acid dimethylamide, (3-amino-phenyl)acetic acid diethyl-amide, (3-amino-phenyl)-acetic acid diallylamide, (3-aminophenyl)-acetic acid N-methyl-butylamide, (3-aminophenyl)-acetic acid N-methyl-allylamide, (3-aminophenyl)-acetic acid N-methyl-benzylamide, (3-aminophenyl)-acetic acid N-methyl-cyclohexylamide, (3-amino-phenyl)-acetic acid N-methyl-anilide, (3-aminophenyl)-acetic acid pyrrolidide, (3-amino-phenyl)-acetic acid piperidide, (3-amino-phenyl)-acetic acid hexamethyleneimide, (3-aminophenyl)-acetic acid morpholide, (3-amino-phenyl)-acetic acid thiamorpholide, (3-amino-phenyl)-acetic acid sulfamorpholide, (3-amino-phenyl)-acetic acid imidazolide-(1), (3-aminophenyl)acetic acid 1,2,4-triazolide-(1) and (3-aminophenyl)-acetic acid benztriazolide.

Hitherto, only some of the compounds of the formula (II) have been described in the literature. The compounds of the formula (II) which have not yet been specifically disclosed can, however, be prepared simply in accordance with customary methods. Thus, for example, aliphatic esters of (3-amino-phenyl)-acetic acid can be obtained by reaction of this acid with alcohols in the presence of hydrogen chloride (Compare J. Amer. Chem. Soc. 39, 2420 (1917) and Ber. 28, 1919 (1885)). The 3-amino-phenyl)acetic acid amides of the formula (II) are accessible from the esters of the formula (II) or their hydrochlorides by reaction with the corresponding amines. Thus, for example, (3-aminophenyl)-acetic acid amide can be prepared by treating (3-aminophenyl)-acetic acid methyl ester hydrochloride with concentrated aqueous ammonia solution (Compare J. Amer. Chem. Soc. 39, 2420 (1917)). A further method which has hitherto been little used but is of almost unlimited diversity, for the synthesis of compounds of the formula (II), is to start from the corresponding (3-nitrophenyl)-acetic acid derivatives and subject these to a reduction with customary reducing agents. Preferred reducing agents for this purpose include metals, such as zinc, tin or iron, in the presence of acids or bases; salts of hydrogen sulphide; metal ions of low valency levels, amongst which $Fe^{2+}$ and $Sn^{2+}$ may be mentioned as examples; catalytically activated hydrogen; and hydrazine. The (3-nitro-phenyl)-acetic acid derivatives required as starting materials in the present instance can be prepared according to methods which are known in principle, for example by reaction of (3-nitro-phenyl)-acetic acid chloride with alcohols, mercaptans or amines (Compare J. Biol. Chem. 68, 504 (1926)).

The formula (III) provides a general definition of the corresponding starting materials which can be used according to the invention.

Q in the formula (III) is preferably chlorine or bromine, or represents an $R^3O$- or $R^3CO-O-$ radical in which $R^3$ has the same preferred meanings as have already been mentioned for $R^3$ in the context of the definition of Z.

The compounds of the formula (III) which can be used as starting materials are already known or can be prepared in a simple manner in accordance with customary methods.

The following may be mentioned as examples of the compounds of the formula (III): acetic anhydride, propionic anhydride, pyrocarbonic acid diethyl ester, acetyl chloride, acetyl bromide, propionyl chloride, isobutyric acid chloride, isovaleric acid chloride, pivalic acid chloride, α-methylvaleric acid chloride, α,α-dimethylvaleric acid chloride, acrylic acid chloride, methacrylic acid chloride, crotonic acid chloride, undecylenic acid chloride, propiolic acid chloride, chloroacetyl chloride, trichloroacetyl chloride, α,α-dichloropropionic acid chloride, α,α-difluoro-propionic acid chloride, phenylacetic acid chloride, 4-chloro-phenylacetic acid chloride, 2,6-dichloro-phenylacetic acid chloride, 4-methylphenylacetic acid chloride, α-naphthylacetic acid chloride, methoxyacetic acid chloride, 2,4-dichlorophenoxy-acetic acid chloride, 2-methyl-4-chlorophenoxy-acetic acid chloride, 2-methyl-4-chlorophenoxy-propionic acid chloride, methylmercaptoacetic acid chloride, 4-chloro-phenylmercapto-acetic acid chloride, cyclopropane-carboxylic acid chloride, cyclopentane-carboxylic acid chloride, cyclohexane-carboxylic acid chloride, 2,6-dichlorobenzoyl chloride, 2,3,6-trichloro-benzoyl chloride, 2-methoxy-3,6-dichloro-benzoyl chloride, 2,5-dichloro-3-nitrobenzoyl chloride, 2,5-dichloro-3-trifluoromethyl-benzoyl chloride, carbonic acid methyl ester chloride, carbonic acid isopropyl ester chloride, carbonic acid 1,1-dimethylbutyl ester chloride, carbonic acid allyl ester chloride, carbonic acid β-chloro-ethyl ester chloride, carbonic acid tetrachloroethyl ester chloride, carbonic acid 2-methoxy-ethyl ester chloride, carbonic acid 2-(2,4-dichloro-phenoxy)-ethyl ester chloride, carbonic acid benzyl ester chloride, carbonic acid 3,4-dichloro-benzyl ester chloride, carbonic acid 3-nitrobenzyl ester chloride, carbonic acid propargyl ester chloride, carbonic acid 4-chloro-butin-(2)-yl ester chloride, thiocarbonic acid O-methyl ester chloride, thiocarbonic acid O-isopropyl ester chloride, thiocarbonic acid O-2,4-dichlorophenoxy-ethyl ester chloride, thiocarbonic acid O-4-chlorobenzyl ester chloride, thiocarbonic acid S-methyl ester chloride, thiocarbonic acid S-ethyl ester chloride, thiocarbonic acid S-butyl ester chloride, thiocarbonic acid S-benzyl ester chloride, dithiocarbonic acid S-methyl ester chloride, dithiocarbonic acid S-isopropyl ester chloride, dithiocarbonic acid S-4-chloro-benzyl ester chloride, dimethylcarbamic acid chloride, diethylcarbamic acid chloride, N-methyl-N-butyl-carbamic acid chloride, diallyl-carbamic acid chloride, N-methyl-N-allyl-carbamic acid chloride, N-methyl-N-(2-methyl-butin-(3)-yl-(2))-cabamic acid chloride, N-methyl-N-cyclopentyl-carbamic acid chloride, N-methyl-N-cyclohexyl-carbamic acid chloride, pyrrolidine-1-carboxylic acid chloride, piperidine-1-carboxylic acid chloride, hexamethyleneimine-1-carboxylic acid chloride, morpholine-4-carboxylic acid chloride, 3,5-dimethyl-morpholine-4-carboxylic acid chloride, thiamorpholine-4-carboxylic acid chloride, sulfamorpholine-4-carboxylic acid chloride, 1-methyl-piperzine-4-carboxylic acid chloride, dimethyl-thiocarbamic acid chloride, diethyl-thiocarbamic acid chloride, diallyl-thiocarbamic acid chloride, N-methyl-N-isopropyl-thiocarbamic acid chloride and N-methyl-N-cyclohexylthiocarbamic acid chloride.

The formula (IV) provides a general definition of the corresponding starting materials which can be used according to the invention. In the formula (IV), $R^5$ has the same preferred meanings as have already been mentioned for $R^5$ in the context of the definition of Z.

The isocyanates or isothiocyanates of the formula (IV) which can be used as starting materials are already known or can be prepared in a simple manner in accordance with customary methods.

The following may be mentioned as examples of such isocyantes and isothiocyanates: methyl isocyanate, ethyl isocyanate, isopropyl isocyanate, sec.-butyl isocyanate, tert.-butyl isocyanate, 2-chloroethyl isocyanate, methoxymethyl isocyanate, allyl isocyanate, propargyl isocyanate, cyclopentyl isocyanate, cyclohexyl isocyanate, methyl isothiocyanate, ethyl isothiocyanate, butyl isothiocyanate, allyl isothiocyanate and cyclohexyl isothiocyanate.

The formula (V) provides a general definition of the corresponding starting materials which can be used according to the invention. In the formula (V), Z has the same preferred meanings as have already been mentioned in defining this substituent. W in the formula (V) is preferably cyano group or the $R^6$—CO— group in which $R^6$ is preferably hydroxyl, halogen (especially chlorine or bromine), optionally chlorine-substituted alkoxy of from 1 to 4 (especially 1 or 2) carbon atoms, or phenoxy which is optionally substituted by fluorine, chlorine, bromine, alkyl of from 1 to 3 carbon atoms and or nitro.

The following may be mentioned as examples of the compounds of the formula (V): 3-(propionylamino)-phenyl-acetonitrile, 3-(propionylamino)-phenyl -acetic acid, 3-(propionylamino)-phenyl -acetic acid chloride, 3-methoxycarbonylamino-) phenyl)-acetic acid, 3-(methoxycarbonylamino)-phenyl -acetonitrile, 3-(methoxycarbonylamino)-phenyl -acetic acid chloride, 3-(N′methyl-ureido)-phenyl-acetonitrile, 3-(N′methyl-ureido)phenyl-acetic acid chloride, 3-(N′-methyl-ureido)-phenylacetic acid methyl ester, 3-(N′-methyl-ureido)-phenyl-acetic acid, 3-(N′,N′-dimethyl-ureido)-phenyl-acetic acid, 3-(N′,N′-dimethyl-ureido)-phenyl-acetonitrile, 3-(N′,N′-dimethylureido)-phenyl-acetic acid chloride and 3-(butylmercaptocarbonylamino)-phenyl -acetic acid chloride.

The compounds of the formula (V) have not previously been disclosed; however, they can be prepared according to the customary methods.

Thus, for example, those compounds of the formula (V) in which Y is cyano may be obtained by reacting 3-amino-phenylacetonitrile either (i) with an acid derivative, especially an acid halide of the formula (III), or (ii) with an isocyanate or isothiocyanate of the formula (IV), in each case optionally in the presence of an inert diluent and optionally in the presence of an acid-binding agent, at temperatures of $-20°$ to $150°$ C, preferably $0°$ to $100°$ C. The reaction products may be isolated in accordance with conventional methods. In those cases in which the reaction is carried out in a water-miscible organic solvent, the compounds of the formula (V) separate out in a crystalline form after merely diluting the reaction mixture with water. 3-Amino-phenyl-acetonitrile, required as a starting material in the above process, is already known (Compare Ber. 17, 506 (1874)).

The compounds of the formula (V), in which W represents a COOH- group, may be obtained, for example, by reacting 3-amino-phenyl-acetic acid either (i) with an acid derivative, especially an acid halide or acid anhydride, of the formula (III), or (ii) with an isocyanate or isothiocyanate of the formula (IV), in each case optionally in the presence of an inert diluent and optionally in the presence of an acid-binding agent, at temperatures of $-20°$ to $150°$ C, preferably $0°$ to $100°$ C. The reaction products may be isolated in accordance with conventional methods. In those cases in which the reaction is carried out in a water-miscible organic solvent, the compounds of the formula (V) separate out in a crystalline form after merely diluting the reaction mixture with water, if necessary after prior acidification. 3-Amino-phenylacetic acid, required as a starting product of the above process, is already known (Compare Ber. 16, 2065 (1873) and J. Amer. Chem. Soc. 39, 1437 (1917)).

The compounds of the formula (V), in which W represents a carboxylic acid alkyl ester group or a carboxylic acid aryl ester group, may be obtained, for example, by reacting a corresponding ester of the formula (II) either (i) with an acid derivative, especially an acid halide or acid anhydride, of the formula (III) or (ii) with an isocyanate or isothiocyanate of the formula (IV), in each case optionally in the presence of an inert diluent and especially in the presence of an acid-binding agent, at temperatures of $-20°$ to $150°$ C, preferably $0°$ C to $100°$ C. The reaction products may be isolated in accordance with conventional methods.

The compounds of the formula (V), in which W represents a halocarbonyl group, may be obtained, for example, by reacting compounds of the formula (V), in which W represents a carboxyl group, with inorganic acid halides, optionally in the presence of an inert diluent, at temperatures of $0°$ to $120°$ C. Working up may be carried out by distilling excess halogenating agent, and any solvent which may be present, from the reaction mixture. The reaction products of the formula (V) are thereby obtained in the form of a crystalline residue.

Preferred inorganic acid halides which can be used in the above reaction for the preparation of particular compounds of the formula (V) include thionyl chloride, phosgene, phosphorus-III halides, phosphorus oxyhalides and phosphorus-V halides.

All organic solvents which are inert towards acid halides can be used as diluents in the halogenation reaction described above. Preferred ones include aliphatic and aromatic hydrocarbons, such as pentene, hexane, petroleum ether, benzine, benzene and toluene; halogenated hydrocarbons, such as methylene chloride and chloroform; ethers, such as diethyl ether and tetrahydrofuran; and ketones, such as acetone. Furthermore, in some cases the inorganic acid halide used in excess, preferably thionyl chloride or phosphorus oxychloride, can serve as the diluent.

The halogenation described above can also be carried out by employing, instead of the compounds of the formula (V), in which W represents a carboxyl group, corresponding salts of these acids, especially their alkali metal salts, alkaline earth metal salts or tert.-amine salts, as starting materials.

In some cases it can be of advantage, in the halogenation described above, to increase the reactivity of the inorganic acid halide by addition of known activators such as, for example, dimethylformamide.

The formula (V) provides a general definition of the corresponding starting materials which can be used according to the invention. In the formula (VI) X has the same preferred meanings as have already been mentioned in defining this substituent.

The alcohols, mercaptans and amines of the formula (VI) which can be used as starting materials are already known, as are the corresponding alkali metal salts of these alcohols and mercaptans.

The following may be mentioned as examples of the compounds of the formula (VI): methanol, ethanol, propanol, isopropanol, tert.-butanol, allyl alcohol, propargyl alcohol, 3-methylbutinol-(3), butenol-(3), 2-chloroethanol, 4-chloro-2-butionol, cyclohexanol, benzyl alcohol, 2,4-dichlorophenol, 4-chlorophenol, methylmercaptan, ethylmercaptan, propylmercaptan, isopropylmercaptan, allylmercaptan, benzylmercaptan, 4-chlorothiophenol, butylmercaptan, methylamine, dimethylamine, ethylamine, diethylamine, isopropylamine, tert.-butylamine, butylamine, cyclohexylamine, cyclopentylamine, aniline, 2-chloro-aniline, 4-chloro-aniline, 2,4-dichloro-aniline, 4-methyl-aniline, 2-methyl-aniline, 4-trifluoromethoxy-aniline, piperidine, pyrrolidine and morpholine.

The following may be mentioned as examples of alkali metal salts of alcohols or mercaptans of the formula (VI): sodium methylate, sodium ethylate, sodium isopropylate, potassium tert.-butylate, sodium phenolate, sodium methyl-mercaptide, sodium ethylmercaptide and sodium n-butylmercaptide.

The formula (VII) provides a general definition of the 3-isocyanato- and 3-isothiocyanato-phenylacetic acid halides which can be used as starting materials according to the invention. In the formula (VII), Hal preferably represents chlorine or bromine, especially chlorine.

The following may be mentioned as examples of such compounds of the formula (VII): 3-isocyanato-phenylacetic acid chloride and 3-isothiocyanato-phenylacetic acid chloride.

The 3-isocyanato- and 3-isothiocyanato-phenylacetic acid halides of the formula (VII) have not previously been disclosed; however, they can be prepared according to processes known in principle (Compare German Patent Specification 1,222,919). Thus, 3-isocyanato- and 3-isothiocyanato- phenylacetic acid chloride may be obtained, for example, by reacting 3-amino-phenylacetic acid with phosgene or tiiosphosgene in an inert organic solvent, such as toluene or chlorobenzene, and in the presence of a stoichiometric amount of quinoline, at temperatures of $-20$ to 150° C. The reaction products are isolated by separating the solvent from the second oily-liquid phase which separates out and subjecting the latter to a distillation under reduced pressure.

The formula (VIII) provides a general definition of the 3-isocyanato- and 3-isothiocyanato-phenylacetic acid derivatives which can be used as starting materials according to the invention. In the formula (VIII), X has the same preferred meanings as have already been mentioned in defining this substituent.

The following may be mentioned individually as examples of the 3-isocyanato- and 3-isothiocyanato-phenylacetic acid derivatives of the formula (VIII): 3-isocyanato-phenylacetic acid methyl ester, 3-isocyanato-phenylacetic acid ethyl ester, 3-isocyanto-phenylacetic acid isopropyl ester, 3-isothiocyanato-phenylacetic acid methyl ester, 3-isothiocyanato-phenylactic acid ethyl ester, 3-isothiocyanato-phenylacetic acid isopropyl ester, 3-isocyanato-phenylacetic acid anilide and 3-isothiocyanato-phenylacetic acid anilide.

The 3-isocyanato- and isothiocyanato-phenylacetic acid derivatives of the formula (VIII) have not previously been disclosed; however, they can be prepared according to processes which are known in principle. They may be obtained, for example, by reacting compounds of the formula (II) or their hydrochlorides with phosgene or thiophosgene in an inert solvent, such as toluene, chlorobenzene or chloroform, at temperatures of $-20°$ C to 150° C. A further possible method of preparation of the isothiocyanatophenylacetic acid derivatives of the formula (VIII) is to react 3-amino-phenyl-acetic acid derivatives of the formula (II) first with carbon disulphide in the presence of bases to give salts of corresponding dithiocarbamic acids and then to convert the latter into the desired compounds of the formula (VIII) with the aid of oxidising agents, for example sodium hypochlorite, heavy metal salts, phosgene or chlorocarbonic acid esters. Working up may be carried out in accordance with customary methods.

The formulae (IX), (X), and (XI) provide a general definition of the corresponding starting materials which can be used according to the invention. In the formulae (IX) and (X), $R^3$ has the same preferred meanings as have already been mentioned for $R^3$ in the context of the definition of Z. In the formula (XI), $R^4$ and $R^5$ have the same prefrred meanings as have already been mentioned for $R^4$ and $R^5$ in the context of the definition of Z.

The alcohols, mercaptans and amines of the formulae (IX), (X) and (XI) which can be used as starting materials are known. Examples of the compounds of the formula (IX), (X) and (XI) include those which have already been mentioned for the compounds of the formula (VI).

In carrying out process variant (a) according to the invention it is possible to use as diluent, both when working according to subvariant ($\alpha$) and when working according to subvariant ($\beta$), any solvent which is inert towards the starting materials of the formulae (III) and (IV) or which does not react more rapidly with these than the reactant of the formula (II). preferred solvents include aliphatic and aromatic hydrocarbons, such as petroleum ether, benzine, cyclohexane, benzene and toluene, halogenated aliphatic or aromatic hydrocarbons, such as methylene chloride, chloroform, carbon tetrachloride and chlorobenzene; ketones, such as acetone and methyl isopropyl ketone; ethers, such as diethyl ether, tetrahydrofuran and dioxan; and esters, such as ethyl acetate, as well as dimethylsulphoxide and dimethylformamide. Sometimes the reaction can also be carried out in an alcohol, such as methanol, ethanol or isopropanol, or in water, as the solvent.

Acid acceptors which can be used in the reaction according to the process variant (a) include all customary acid-binding agents. Preferred ones include alkali metal carbonates, alkaline earth metal carbonates, alkali metal hydroxides, alkaline earth metal hydroxides, alkaline earth metal oxides, alkali metal alcoholates and tertiary amines. The following may be mentioned as being particularly suitable examples: sodium carbonate, potassium carbonate, triethyl-amine, N,N-dimethylaniline, N,N-dimethylbenzylamine, pyridine and quinoline.

In carrying out process variant (a), the reaction temperature can be varied within a substantial range. In general, the reaction is carried out at $-20°$ to 150° C, preferably 0° to 100° C.

The reaction according to process variant (a) can be carried out under normal pressure or under elevated pressure. In general, it is carried out under normal pressure.

In carrying out process variant (a), preferably 1 to 1.5 mols of starting compound of the formula (III) or (IV) and, where appropriate, a stoichiometric amount or an excess of acid-binding agent, are employed per mol of starting material of the formula (III). If an amine base is used as the acid acceptor, this base can at the same time serve as the solvent; in that case, the amine base should, however, be used in larger excess, exceeding the stoichiometric amount. This method of working is particularly advisable if the reactant of the formula (III) is an acid halide which reacts relatively sluggishly, for example a carbamic acid halide. If an acid anhydride is used as the starting material of the formula (III), the addition of an acid acceptor can as a rule be dispensed with. Furthermore, the acid anhydride itself can act as a solvent; for this purpose, it has to be added in such amount as to ensure homogeneous mixing of the reaction batches.

To isolate the compounds of the formula (I) in process variant (a), salts which may have been produced may be first filtered off from the reaction mixture. The filtrate may then be concentrated by distilling off the solvent. The residue which thereupon remains may be purified either by recrystallisation or by distillation. If the reaction is carried out in a water-miscible organic solvent, for example acetone, the compounds of the formula (I) may separate out in a crystalline form after merely diluting the reaction mixture with water. In some cases, especially in the reaction of compounds of the formula (II) with isocyanates or isothiocyanates of the formula (IV), the reaction products may be obtained in a crystalline form merely after cooling the reaction mixture.

In carrying out process variant (b), all inert solvents can be used as diluents The preferred ones include those solvents which have already been mentioned as being preferred in process variant (a).

Acid acceptors which can be used in the reaction according to process variant (b) of the invention include all customary acid-binding agents. Preferred ones include those acid-binding agents which have already been mentioned as being preferred in process varient (a). Sometimes an amine component of the formula (VI), if present in excess, can also serve as the acid acceptor.

In the reaction according to process variant (b), the reaction temperatures can be varied in a similar manner to the case of process variant (a).

The reaction according to process variant (b) can be carried out under normal pressure or under elevated pressure. In general, it is carried out under normal pressure.

If an acid or a nitrile of the formula (V) is reacted with an alcohol of the formula (VI) in process variant (b) the addition of acid catalysts may be necessary. Preferred acid catalysts include inorganic acids, for example hydrochloric acid or sulphuric acid.

In carrying out process varient (b), preferably 1 mol or an excess of an alcohol, mercaptan or amine of the formula (VI), or of an alkali metal salt of an alcohol or mercaptan of the formula (VI), is employed per mol of starting compound of the formula (V), together with, where appropriate, a stoichiometric amount or an excess of acid-binding agent or, where appropriate, a small amount of an acid catalyst.

In the reaction according to process variant (b), the reaction products may be isolated in accordance with the customary methods.

As a rule, the reaction mixture is worked up in the way already described for process variant (a).

In carrying out process variant (c), all inert solvents can be used as diluents. Preferred ones include those solvents which have already been mentioned as being preferred in process variant (a). Sometimes, the amines which function as reactants, or water, can be used as the solvent.

Acid acceptors which can be used in the reaction according to process variant (c) are all customary acid-binding agents. Preferred ones include those acid-binding agents which have already been mentioned as being preferred in process variant (a). Sometimes an amine component of the formula (VI), if present in excess, can serve as the acid acceptor.

In the reaction according to process variant (c), the reaction temperatures can be varied within a substantial range. In general, the reaction is carried out at $-20°$ to $150°$ C, preferably $-5°$ to $100°$ C.

The reaction according to process varient (c) can be carried out under normal pressure or under elevated pressure. In general, it is carried out under normal pressure.

In carrying out process variant (c), at least 2 mols of an alcohol, mercaptan or amine of the formula (VI) and, if appropriate, 1 mol or an excess of acid-binding agent, are generally employed per mol of starting compound of the formula (VII).

In the reaction according to process variant (c) of the invention, the reaction products may be isolated by customary methods. As a rule, the reaction mixture is worked up in the way which has already been described for process varient (a).

Since, in the compounds of the formula (VII), there is very little graduation between the reactivity of the isocyanate group and that of the halocarbonyl group, the process variant (c) is preferably used when it is intended to prepare compounds of the formula (I) in which the radicals Z and X are identical.

In carrying out process variant (d), all inert solvents can be used as diluents. Preferred ones include the solvents which have already been mentioned as being preferred in process variant (a). Sometimes the alcohols which function as reactants can also be used as solvents.

In the reaction according to process variant (d), the reaction temperatures can be varied similarly to the case of variant (c).

The reaction according to process variant (d) can be carried out under normal pressure or under elevated pressure. In general, it is carried out under normal pressure.

If, in process variant (d), a compound of the formula (VIII) is reacted with an alcohol of the formula (IX) or with a mercaptan of the formula (X), it is advisable to add a basic catalyst. Preferred catalysts for this purpose are alkali metal hydroxides, alkali metal alcoholates, alkaline earth oxides, alkaline earth metal hydroxides or tertiary amines.

In carrying out process variant (d) according to the invention, preferably 1 mol, or a slight excess, of alcohol of the formula (IX) or mercaptan of the formula (X) or amine of the formula (XI) is employed per mol of starting compound of the formula (VIII), where appropriate together with a small amount of a basic catalyst.

In the reaction according to process variant (d), the reaction products may be isolated by customary methods.

As a rule, the reaction mixture is worked up as has already been described for the case of process variant (a).

The following may be mentioned as specific examples of the 3-amino-phenyl-acetic acid derivatives according to the invention, of the formula (I): 3-N',N'-dimethyl-ureido-phenylacetic acid methyl ester, 3-N',N'-dimethyl-ureido-phenylacetic acid ethyl ester, 3-N', N'-dimethyl-ureido-phenylacetic acid isopropyl ester, 3-N', N'-dimethyl-ureido-phenylacetic acid butyl ester, 3-N',N'-dimethyl-ureido-phenylacetic acid hexyl ester, 3-N', N'-dimethyl-ureido-phenylacetic acid allyl ester, 3-N', N'-dimethyl-ureido-phenylacetic acid crotyl ester, 3-N', N'-dimethyl-ureido-phenylacetic acid propargyl ester, 3-N', N'-dimethyl-ureido-phenylacetic acid 3-methyl-butin-(1)-yl-(3) ester, 3-N', N'-dimethyl-ureido-phenylacetic acid 2-chloro-ethyl ester, 3-N', N'-dimethyl-ureido-phenylacetic acid 1,2,2,2-tetrachloroethyl ester, 3-N', N'-dimethyl-ureido-phenylacetic acid 2-ethoxy-ethyl ester, 3-N', N'-dimethyl-ureido-phenylacetic acid 2-phenoxy-ethyl ester, 3-N', N'-dimethyl-ureido-phenylacetic acid 2-(2,4-dichloro-phenoxy)-ethyl ester, 3-N', N'-dimethyl-ureido-phenylacetic acid 2-phenylmercapto-ethyl ester, 3-N', N'-dimethyl-ureido-phenylacetic acid 2-methylmercapto-ethyl ester, 3-N', N'-dimethyl-ureido-phenylacetic acid benzyl ester, 3-N',N'-dimethyl-ureido-phenylacetic acid 4-chloro-benzyl ester, 3-N',N'-dimethyl-ureido-phenylacetic acid 2-(4-methyl-phenyl)-ethyl ester, 3-N',N'-dimethyl-ureido-phenylacetic acid 4-trifluoromethyl-benzyl ester, 3-N',N'-dimethyl-ureido-phenylacetic acid 4-methoxy-benzyl ester, 3-N',N'-dimethyl-ureido-phenylacetic acid 4-methylmercapto-benzyl ester, 3-N',N'-dimethyl-ureido-phenylacetic acid, 4-nitro-benzyl ester, 3-N',N'-dimethyl-ureido-phenylacetic acid α-naphthylmethyl ester, 3-N',N'-dimethyl-ureido-phenylacetic acid cyclobutyl ester, 3-N',N'-dimethyl-ureido-phenylacetic acid cyclopentyl ester, 3-N',N'-dimethyl-ureido-phenylacetic acid cyclohexyl ester, 3-N',N'-dimethyl-ureido-phenylacetic acid 4-methyl-cyclohexyl ester, 3-N',N'-dimethyl-ureido-thiophenylacetic acid S-methyl ester, 3-N',N'-dimethyl-ureido-thiophenylacetic acid S-isopropyl ester, 3-N',N'-dimethyl-ureido-thiophenylacetic acid S-butyl ester, 3-N',N'-dimethyl-ureido-thiophenylacetic acid S-allyl ester, 3-N',N'-dimethyl-ureido-thiophenylacetic acid S-benzyl ester, 3-N',N'-dimethyl-ureido-thiophenylacetic acid S-4-chlorobenzyl ester, 3-N',N'-dimethyl-ureido-thiophenylacetic acid S-cyclohexyl ester, 3-N',N'-dimethyl-ureido-phenylacetic acid methylamide, 3-N',N'-dimethyl-ureido-phenylacetic acid ethylamide, 3-N',N'-dimethyl-ureido-phenylacetic acid propylamide, 3-N',N'-dimethyl-ureido-phenylacetic acid isopropylamide, 3-N',N'-dimethyl-ureido-phenylacetic acid butylamide, 3-N',N'-dimethyl-ureido-phenylacetic acid isobutylamide, 3-N',N'-dimethyl-ureido-phenylacetic acid sec.-butylamide, 3-N',N'-dimethyl-ureido-phenylacetic acid tert.-butylamide, 3-N',N'-dimethyl-ureido-phenylacetic acid pentylamide, 3-N',N'-dimethyl-ureido-phenylacetic acid 1-methyl-butylamide, 3-N',N'-dimethyl-ureido-phenylacetic acid 1-methylisobutylamide, 3-N',N'-dimethyl-ureido-phenylacetic acid 3-methyl-butylamide, 3-N',N'-dimethyl-ureido-phenylacetic acid 1-ethyl-propylamide, 3-N',N'-dimethyl-ureido-phenylacetic acid dodecylamide, 3-N',N'-dimethyl-ureido-phenylacetic acid allylamide, 3-N',N'-dimethyl-ureido-phenylacetic acid propargylamide, 3-N',N'-dimethyl-ureido-phenylacetic acid 3-methyl-butin-(1)-yl-(3)-amide, 3-N',N'-dimethyl-ureido-phenylacetic acid 2-chloroethylamide, 3-N',N'-dimethyl-ureido-phenylacetic acid 3-cyano-propylamide, 3-N',N'-dimethyl-ureido-phenylacetic acid 2-cyano-propyl-(2)-amide, 3-N',N'-dimethyl-ureido-phenylacetic acid carboethoxy-methylamide, 3-N',N'-dimethyl-ureido-phenylacetic acid 2-carbomethoxy-ethylamide, 3,-N',N'-dimethyl-ureido-phenylacetic acid N,N-dimethyl-carbamoyl-methylamide, 3-N',N'-dimethyl-ureido-phenylacetic acid 2-ethoxy-ethylamide, 3-N',N'-dimethyl-ureido-phenylacetic acid 3-methoxy-propylamide, 3-N',N'-dimethyl-ureido-phenylacetic acid 2-phenoxyethylamide, 3-N',N'-dimethyl-ureido-phenylacetic acid 2-methylmercapto-ethylamide, 3-N',N'-dimethyl-ureido-phenylacetic acid 2-phenylmercapto-ethylamide, 3-N',N'-dimethyl-ureido-phenylacetic acid 2-methylsulphonyl-ethylamide, 3-N',N'-dimethyl-ureido-phenylacetic acid 2-phenylsulphonyl-ethylamide, 3-N',N'-dimethyl-ureido-phenylacetic acid benzylamide, 3-N',N'-dimethyl-ureido-phenylacetic acid 4-chloro-benzylamide, 3-N',N'-dimethyl-ureido-phenylacetic acid 2,6-dichloro-benzylamide, 3-N',N'-dimethyl-ureido-phenylacetic acid 4-methyl-benzylamide, 3-N',N'-dimethyl-ureido-phenylacetic acid 4-trifluoromethyl-benzylamide, 3-N',N'-dimethyl-ureido-phenylacetic acid 4-methoxy-benzylamide, 3-N',N'-dimethyl-ureido-phenylacetic acid 4-methylmercapto-benzylamide, 3-N',N'-dimethyl-ureido-phenylacetic acid 4-nitro-benzylamide, 3-N',N'-dimethyl-ureido-phenylacetic acid 1-phenyl-ethylamide, 3-N',N'-dimethyl-ureido-phenylacetic acid 1,1-dimethyl-benzylamide, 3-N',N'-dimethyl-ureido-phenylacetic acid α-naphthylmethylamide, 3-N',N'-dimethyl-ureido-phenylacetic acid cyclopropyl-methylamide, 3-N',N'-dimethyl-ureido-phenylacetic acid cyclopentyl-methylamide, 3-N',N'-dimethyl-ureido-phenylacetic acid cyclohexyl-methylamide, 3-N',N'-dimethyl-ureido-phenylacetic acid cyclopropylamide, 3-N',N'-dimethyl-ureido-phenylacetic acid cyclopentylamide, 3-N',N'-dimethyl-ureido-phenylacetic acid cyclohexylamide, 3-N',N'-dimethyl-ureido-phenylacetic acid 4-methyl-cyclohexylamide, 3-N',N'-dimethyl-ureido-phenylacetic acid 3,3,5-trimethylcyclohexylamide, 3-N',N'-dimethyl-ureido-phenylacetic acid anilide, 3-N',N'-dimethyl-ureido-phenylacetic acid 3-chloro-anilide, 3-N',N'-dimethyl-ureido-phenylacetic acid 4-chloro-anilide, 3-N',N'-dimethyl-ureido-phenylacetic acid 3,4-dichloro-anilide, 3-N',N'-dimethyl-ureido-phenylacetic acid 3-nitro-anilide, 3-N',N'-dimethyl-ureido-phenylacetic acid 4-nitro-anilide, 3-N',N'-dimethyl-ureido-phenylacetic acid 4-cyano-anilide, 3-N',N'-dimethyl-ureido-phenylacetic acid 4- carboethoxy-anilide, 3-N',N'-dimethyl-ureido-phenylacetic acid 4-carbamoyl-anilide, 3-N',N'-dimethyl-ureido-phenylacetic acid 3-methyl-anilide, 3-N',N'-dimethyl-ureido-phenylacetic acid 4-methyl-anilide, 3-N',N'-dimethyl-ureido-phenylacetic acid 3-chloro-4-methylanilide, 3-N',N'-dimethyl-ureido-phenylacetic acid 4-chloro-3-methylanilide, 3-N',N'-dimethyl-ureido-phenylacetic acid 4-isopropyl-anilide, 3-N',N'-dimethyl-ureido-phenylacetic acid 4-tert.-butyl-anilide, 3-N',N'-dimethyl-ureido-phenylacetic acid 4-cyclohexyl-anilide, 3-N',N'-dimethyl-ureido-phenyacetic acid 4-methoxy-anilide, 3-N',N'-dimethyl-ureido-phenylacetic acid 3-chloro-4-methoxy-anilide, 3-N',N'-dimethyl-ureido-phenylacetic acid 4-methylmercaptoanilide, 3-N',N'-dimethyl-ureido-phenylacetic acid 3-chloro-4-methylmercapto-anilide, 3-N'N'-dimethyl-ureido-phenylacetic acid 3-chloro-4-phenylmercapto-anilide, 3-N',N'-dimethyl-ureido-phenylacetic acid 3-chloro-4-methylsulphonyl-anilide, 3-N',N'-dimethyl-ureido-phenylacetic acid 3-chloro-4-phenylsulphonyl-anilide, 3-N',N'-dimethyl-ureido-phenylacetic acid 3-trifluoromethyl-anilide, 3-N',N'-dimethyl-ureido-phenylacetic acid 3-chloro-4-trifluoromethyl-anilide, 3-N',N'-dimethyl-ureido-phenylacetic acid 4-thiocyanato-anilide 3-N',N'-dimethyl-ureido-phenylacetic acid α-naphthylamide, 3-N',N'-dimethyl-ureido-phenylacetic acid dimethylamide, 3-N',N'-dimethyl-ureido-phenylacetic acid diethylamide, 3-N',N'-dimethyl-ureido-phenylacetic acid diallylamide, 3-N',N'-dimethyl-ureido-phenylacetic acid N-methyl-isopropylamide, 3-N',N'-dimethylureido-phenylacetic acid N-methyl-butylamide, 3-N',N'-dimethyl-ureido-phenylacetic acid N-methyl-allylamide, 3-N',N'-dimethyl-ureido-phenylacetic acid N-methyl-benzylamide, 3-N',N'-dimethyl-ureido-phenylacetic acid N-methyl-cyclohexyl-amide, 3-N',N'-dimethyl-ureido-phenylacetic acid N-methyl-anilide, 3-N',N'-dimethyl-ureido-phenylacetic acid N-methyl-4-chloro-anilide, 3-N',N'-dimethyl-ureido-phenylacetic acid furfurylmethylamide, 3-N',N'-dimethyl-ureido-phenylacetic acid thienyl-(2)-amide, 3-N',N'-dimethyl-ureido-phenylacetic acid thienyl-(3)-amide, 3-N',N'-dimethyl-ureido-phenylacetic acid pyranyl-(2)-methylamide, 3-N',N'-dimethyl-ureido-phenylacetic acid pyridyl-(2)-amide, 3-N',N'-dimethyl-ureido-phenylacetic acid 1,3-thiazolyl-(2)-amide, 3-N',N'-dimethyl-ureido-phenylacetic acid benz-(1,3)-oxazol-(2)-amide, 3-N',N'-dimethyl-ureido-phenylacetic acid benz-(1,3)-thiazolyl-(2)-amide, 3-N',N'-dimethyl-ureido-phenylacetic acid 5-tert.-butyl-1,3,4-thiadiazolyl-(2)-amide, 3-N',N'-dimethyl-ureido-phenylacetic acid 5-trifluoromethyl-1,3,4-thiadiazolyl-(2)-amide, 3-N',N'-dimethyl-ureido-phenyacetic acid 5-methylsulphonyl-1,3,4-thiadiazolyl-(2)-amide, 3-N',N'-dimethyl-ureido-phenylacetic acid 1,2,4-triazolyl-(3)-amide, 3-N',N'-dimethyl-ureido-phenylacetic acid pyrrolidide, 3-N',N'-dimethyl-ureido-phenylacetic acid piperidide, 3-N',N'-dimethyl-ureido-phenylacetic acid hexamethyleneimide, 3-N',N'-dimethyl-ureido-phenylacetic acid N-methyl-piperazide, 3-N',N'-dimethyl-ureido-phenylacetic acid 1,2,3,4-tetrahydroquinolide, 3-acetamido-phenylacetic acid isopropyl ester, 3-propionamido-phenylacetic acid sec.-butylamide, 3-isobutyramidophenylacetic acid tert.-butylamide, 3-α,α-dimethyl-valerylamido-phenylacetic acid anilide, 3-α-methyl-valerylamidophenylacetic acid anilide, 3-methacrylamido-phenylacetic acid sec.-butylamide, 3-propiolamido-phenylacetic acid sec.-butylamide, 3-chloroacetamido-phenylacetic acid sec.-butylamide, 3-trichloroacetamido-phenylacetic acid sec.-butylamide, 3-α,α-dichloro-propionamido-phenylacetic acid sec.-butylamide, 3-(2,6-dichloro-phenylacetamido)-phenylacetic acid sec.-butylamide, 3-α-naphthylacetamido phenylacetic acid sec.-butylamide, 3-methocyacetamido-phenylacetic acid sec.-butylamide, 3-(2,4-dichloro-phenoxy-acetamido)-phenylacetic acid, sec.-butylamide, 3-(2-methyl-4-chloro-phenoxy-acetamido)-phenylacetic acid, sec.-butylamide, 3-(α-2-methyl-4-chloro-phenoxy-propionamido)-phenylacetic acid sec.-butylamide, 3-methylmercaptoacetamido-phenylacetic acid sec.-butylamide, 3-phenyl-mercaptoacetamido-phenylacetic acid sec.-butylamide, 3-cyclopropanecarbonamido-phenylacetic acid sec.-butylamide, 3-cyclohexanecarbonamido-phenylacetic acid sec.-butylamide, 3-(2,6-dichlorobenzamido-phenylacetic acid sec.-butylamide, 3-(2-methoxy-3,6-dichloro-benzamido)-phenylacetic acid sec.-butylamide, 3-(4-trifluoromethyl-benzamido)-phenylacetic acid sec.-butylamide, 3-(3-nitro-benzamido)-phenylacetic acid sec.-butylamide, 3-methoxycarbonylamino-phenylacetic acid cyclohexylamide, 3-isopropoxycarbonylamino-phenylacetic acid cyclohexylamide, 3-hexyloxy-carbonylamino-phenylacetic acid cyclohexylamide, 3-allyloxy-carbonyl-amino-phenylacetic acid cyclohexylamide, 3-(2-chloro-ethoxy)carbonylamino-phenylacetic acid cyclohexylamide, 3-(2-ethoxy-ethoxy)-carbonylamino-phenylacetic acid cyclohexylamide, 3-(2-phenoxy-ethoxy)-carbonylamino-phenylacetic acid cyclohexylamide, 3-[2,4-dichlorophenoxy)-ethoxy-carbonylamino]-phenylacetic acid cyclohexyl-amide, 3-(3,4-dichloro-benzyloxy-carbonylamino)-phenylacetic acid cyclohexylamide, 3-propargyloxy-carbonylaminophenyl-acetic acid cyclohexylamide, 3-methoxy-thiocarbonylaminophenylacetic acid anilide, 3-isopropoxy-thiocarbonylamino-phenylacetic acid anilide, 3-allyloxy-thiocarbonylamino-phenylacetic acid anilide, 3-butylmercapto-carbonylamino-phenylacetic acid tert.-butylamide, 3-benzylmercapto-carbonylamino-phenylacetic acid tert.-butylamide, 3-(4-chloro-benzylmercapto)-carbonyl-amino-phenylacetic acid tert.-butyl-amide, 3-ethylmercapto-thiocarbonylaminophenylacetic acid tert.-butylamide, 3-N'-methyl-ureido-phenylacetic acid sec.-butylamide, 3-N'-methyl-ureido-phenylacetic acid anilide, 3-N'-methyl-ureido-phenylacetic acid 3-methylanilide, 3-N'-methyl-ureido-phenylacetic acid cyclohexylamide, 3-N'-methyl-ureido-phenylacetic acid isopropyl ester, 3-N'-ethyl-ureido-phenylacetic acid anilide, 3-N'-butyl-ureido-phenylacetic acid anilide, 3-N'-allyl-ureido-phenylacetic acid anilide, 3-N'-methallyl-ureido-phenylacetic acid anilide, 3-N'-propinyl-ureido-phenylacetic acid anilide, 3-N'-(3-methyl-butin-(1)-yl-(3))-ureido-phenylacetic acid anilide, 3-N'-cyclopentyl-ureido-phenylacetic acid anilide, 3-N'-cyclohexyl-ureido-phenylacetic acid anilide, 3-N',N'-diethyl-ureido-phenylacetic acid anilide, 3-N',N'-diallyl-ureido-phenylacetic acid anilide, 3-N'-methyl-N'-isopropyl-ureido-phenylacetic acid anilide, 3-N'-methyl-N'-butyl-ureido-phenylacetic acid anilide, 3-N'-methyl-N'-allyl-ureido-phenylacetic acid anilide, 3-N'-methyl-N'-cyclohexyl-ureido-phenylacetic acid anilide, 3-N',N'-cyclotetramethylene-ureido-phenylacetic acid anilide, 3-N',N'-cyclopentamethylene-ureido-phenylacetic acid anilide, 3-N',N'-cyclohexamethylene-ureido-phenylacetic acid anilide, 3-morpholino-(1)-carbamido-phenylacetic acid anilide, 3-thiamorpholino-(1)-carbamido-phenylacetic acid anilide, 3-sulpha-morpholino-(1)-carbamido-phenylacetic acid anilide and 3-(4-methyl-piperazino-(1)-carbamido)-phenylacetic acid anilide.

EXAMPLE 1

Preparation of 3-propionylaminophenyl-acetic acid anilide

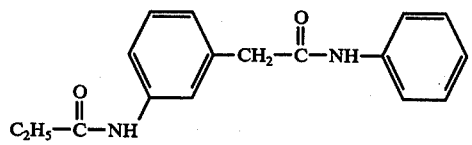

Process (a)

9.25 g (0.1 mol) of propionic acid chloride were added dropwise, at 20° to 25° C, to a solution of 22.6 g (0.1 mol) of 3-amino-phenylacetic acid anilide and 10.1 g (0.1 mol) of triethylamine in 200 ml of acetone, whilst cooling. The mixture was stirred for a further hour at room temperature and was then diluted with 500 ml of water. The crystals which precipitated were filtered off and recrystallized from ethyl acetate. 23.1 g (82% of theory) of 3-propionylaminophenylacetic acid anilide of melting point 159°–160° C were obtained.

Process (b)

20.7 g (0.1 mol) of 3-propionylamino-phenylacetic acid of melting point 114° C were boiled in 125 ml of thionyl chloride until a clear liquid had formed. The excess thionyl chloride was entirely distilled off, after which the 3-propionylaminophenylacetic acid chloride remained as a crystalline residue. This residue was dissolved in 100 ml of acetone and the solution was added dropwise, whilst cooling at 20° to 25° C, to a mixture 18.6 g (0.2 mol) of aniline of 50 ml of acetone. The mixture was stirred for a further 2 hours at room temperature and was then diluted with 500 ml of water. The crystals which separated out were filtered off, dried and recrystallized from ethyl acetate. 24.8 g (88% of theory) of 3-propionylamino-phenylacetic acid anilide of melting point 159°-160° C were obtained.

The 3-propionylamino-phenylacetic acid required as a starting product was prepared analogously to the information in J. Biol. Chem. 68, 507 (1926).

added dropwise to a solution of 20.6 g (0.1 mol) of 3-amino-phenylacetic acid tert.-butylamide in 200 ml of acetone whilst cooling at 15 to 20° C. The mixture was stirred for a further 2 hours at room temperature, the triethylamine hydrochloride which had precipitated was filtered off and the filtrate was concentrated by evaporation under reduced pressure. The residue which hereupon remained was stirred with very dilute hydrochloric acid, filtered off, dried and recrystallized from a little carbon tetrachloride. 22 g (83.5% of theory) of 3-methoxycarbonylamino-phenylacetic acid tert.-butylamide of melting point 123°-124° C were obtained.

The active compounds listed in Table 1 which follow were prepared analogously:

Table 1

$$\underset{\underset{Z-\overset{\overset{Y}{\|}}{C}-NH}{}}{\text{phenyl}}-CH_2-\overset{\overset{O}{\|}}{C}-X$$

| Example No. | X | Y | Z | Melting point [° C] | Substance recrystallised from |
|---|---|---|---|---|---|
| 3 | $-NH-C(CH_3)_3$ | O | $C_2H_5$ | 172-174 | Ethyl acetate |
| 4 | $-NH-\langle H \rangle$ | O | $C_2H_5$ | 146-148 | Toluene |
| 5 | $-NH-\langle \rangle-Cl$ | O | $C_2H_5$ | 203 | Ethanol |
| 6 | $-NH-\langle H \rangle$ | O | $OCH_3$ | 161-163 | Toluene |
| 7 | $-NH-\langle \rangle$ | O | $OCH_3$ | 137-138 | Ethyl acetate |
| 8 | $-NH-\langle \rangle$ | O | $CH_2Cl$ | 175-177 | Butanol |
| 9 | $-NH-\langle \rangle$ | O | $CCl_3$ | 163 | Ethanol |
| 10 | $-NH-\langle \rangle$ | O | $-CH(CH_3)_2$ | 184-186 | Ethanol |
| 11 | $-NH-C(CH_3)_3$ | O | $-CH_2Cl$ | 192-194 | Ethanol |
| 12 | $-NH-C(CH_3)_3$ | O | $-CH(CH_3)_2$ | 188-190 | Ethanol |
| 13 | $-NH-\langle \rangle$ | O | $-SC_2H_5$ | 136-138 | Ethyl acetate/ Ligroin |

EXAMPLE 2

Preparation of 3-methoxycarbonylamino-phenylacetic acid tert.-butylamide

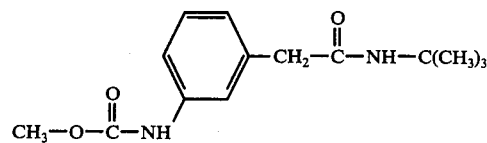

10.45 g (0.1 mol) of chloroformic acid methyl ester, followed by 10.1 g (0.1 mol) of triethylamine, were

EXAMPLE 14

Preparation of 3-(N'-methylureido)-phenylacetic acid methylamide

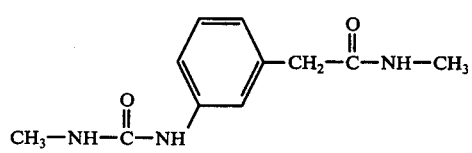

0.1 g of triethylenediamine, followed by 5.7 g (0.1 mol) of methyl isocyanate, was added to a solution of 16.4 g (0.1 mol) of 3-amino-phenylacetic acid methylamide in 100 ml of dioxane at room temperature. The mixture was stirred for a further 3 hours at 40° to 50° C. After cooling, the crystalline precipitate which had separated out was filtered off and dried. After recrystallization from ethanol, 19.5 g (88% of theory) of 3-(N'-methylureido)-phenylacetic acid methylamide of melting point 175°-177° C were obtained.

The active compounds listed in Table 2 which follows were prepared analogously:

Example 28

Preparation of 3-(N',N'-dimethylureido)-phenylacetic acid sec.-butylamide

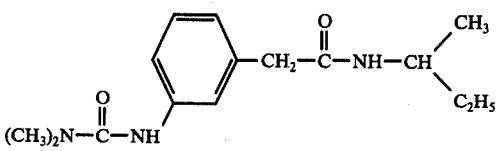

20.6 g (0.1 mol) of 3-amino-phenylacetic acid sec.-butylamide were dissolved in 100 ml of pyridine. 10.75 g (0.1 mol) of dimethylcarbamic acid chloride were added thereto. The mixture was stirred for a further 2 hours at room temperature and 2 hours at 50° to 60° C.

Table 2

| Example No. | X | Y | Z | Melting point [° C] | Substance recrystallised from |
|---|---|---|---|---|---|
| 15 | —NH—CH₂—CH(CH₃)CH₃ | O | —NH—CH₃ | 171–173 | Ethanol |
| 16 | —NH—C(CH₃)₃ | O | —NH—CH₃ | 175–177 | Ethanol |
| 17 | —NH—(cyclohexyl) | O | —NH—CH₃ | 194 | Ethanol |
| 18 | —NH—(phenyl) | O | —NH—CH₃ | 194–196 | Butanol |
| 19 | —NH—(phenyl-CH₃) | O | —NH—CH₃ | 191–193 | Ethanol |
| 20 | —NH—(phenyl-Cl) | O | —NH—CH₃ | 227 | Dimethyl-formamide/methanol |
| 21 | —NH—(phenyl) | S | —NH—CH₃ | 194 | Butanol |
| 22 | —NH—CH(CH₃)—(phenyl) | O | —NH—CH₃ | 163–165 | Ethanol |
| 23 | —NH—(phenyl-Cl) | O | —NH—CH₃ | 175 | Butanol |
| 24 | —NH—(phenyl-OCH₃, Cl) | O | —NH—CH₃ | 204 | Butanol |
| 25 | —NH—(phenyl-Cl, Cl) | O | —NH—CH₃ | 228–230 | Glycol-monomethylether |
| 26 | —NH—(phenyl-OCH₃) | O | —NH—CH₃ | 201–203 | Glycol-monomethylether |
| 27 | —NH—(phenyl-CF₃) | O | —NH—CH₃ | 194–196 | Ethanol |

The residue which remained after distilling off the pyridine under reduced pressure was stirred with very dilute hydrochloric acid, filtered off and then recrystallized from butyl acetate. 17 g (61.5% of theory) of 3-(N',N'-dimethylureido)-phenylacetic acid sec.-butylamide of melting point 170–171° C were obtained.

The active compounds listed in Table 3 which follows were prepared analogously:

Table 3

Structure:

3-substituted phenyl with $CH_2-C(=O)-X$ group and $Z-C(=Y)-NH-$ substituent

| Example No. | X | Y | Z | Melting point [° C] | Substance recrystallised from |
|---|---|---|---|---|---|
| 29 | OCH$_3$ | O | N(CH$_3$)$_2$ | 167–168 | Petroleum ether |
| 30 | O—CH(CH$_3$)$_2$ | O | N(CH$_3$)$_2$ | 90–92 | Petroleum ether |
| 31 | NH—CH$_3$ | O | N(CH$_3$)$_2$ | 128–130 | Dioxane |
| 32 | N(CH$_3$)$_2$ | O | N(CH$_3$)$_2$ | 81–83 | |
| 33 | NH—C$_2$H$_5$ | O | N(CH$_3$)$_2$ | 118–120 | Ethyl acetate |
| 34 | N(C$_2$H$_5$)$_2$ | O | N(CH$_3$)$_2$ | 46–48 | |
| 35 | NH—C$_3$H$_7$ | O | N(CH$_3$)$_2$ | 150–151 | Ethyl acetate |
| 36 | NH—i-C$_3$H$_7$ | O | N(CH$_3$)$_2$ | 168–170 | Ethyl acetate |
| 37 | NH—C$_4$H$_9$ | O | N(CH$_3$)$_2$ | 128–130 | Ethyl acetate |
| 38 | NH—CH$_2$—CH(CH$_3$)$_2$ | O | N(CH$_3$)$_2$ | 150–151 | Ethyl acetate |
| 39 | NH—C(CH$_3$)$_3$ | O | N(CH$_3$)$_2$ | 200 | Ethanol |
| 40 | NH—C$_6$H$_{11}$ (cyclohexyl) | O | N(CH$_3$)$_2$ | 208–210 | Ethanol |
| 41 | NH—C$_6$H$_5$ | O | N(CH$_3$)$_2$ | 158–160 | Ethanol |
| 42 | NH—C$_6$H$_4$—CH$_3$ | O | N(CH$_3$)$_2$ | 186–188 | Ethanol |

Table 3-continued

Structure:

$$Z-\underset{\underset{NH}{|}}{\overset{\overset{Y}{\|}}{C}}-\text{[3-substituted phenyl]}-CH_2-\overset{O}{\overset{\|}{C}}-X$$

| Example No. | X | Y | Z | Melting point [°C] | Substance recrystallised from |
|---|---|---|---|---|---|
| 43 | NH—C$_6$H$_4$—CH$_3$ (p) | O | N(CH$_3$)$_2$ | 155–157 | Ethyl acetate |
| 44 | NH—C$_6$H$_4$—Cl (m) | O | N(CH$_3$)$_2$ | 146–148 | Ethyl acetate |
| 45 | NH—CH$_2$—CH(C$_2$H$_5$)(C$_4$H$_9$) | O | N(CH$_3$)$_2$ | 70–72 | Ethyl acetate |
| 46 | NH—C$_{12}$H$_{25}$ | O | N(CH$_3$)$_2$ | 176–178 | Butanol |
| 47 | NH—CH$_2$—CH=CH$_2$ | O | N(CH$_3$)$_2$ | 113–115 | Ethyl acetate |
| 48 | NH—CH$_2$—CH$_2$—OCH$_3$ | O | N(CH$_3$)$_2$ | 128–130 | Toluene |
| 49 | NH—(CH$_2$)$_3$—OCH$_3$ | O | N(CH$_3$)$_2$ | 120–121 | Ethyl acetate |
| 50 | NH—CH$_2$—CH$_2$—O—C$_6$H$_5$ | O | N(CH$_3$)$_2$ | 125 | Ethyl acetate/ether |
| 51 | NH—CH$_2$—C$_6$H$_{11}$ | O | N(CH$_3$)$_2$ | 182–184 | Ethanol |
| 52 | NH—CH$_2$—C$_6$H$_5$ | O | N(CH$_3$)$_2$ | 160 | Butyl acetate |
| 53 | NH—C$_6$H$_4$—Cl (o) | O | N(CH$_3$)$_2$ | 159–161 | Butanol |
| 54 | NH—C$_6$H$_3$—Cl$_2$ (2,3) | O | N(CH$_3$)$_2$ | 196–198 | Butanol |
| 55 | NH—C$_6$H$_3$—Cl$_2$ (3,4) | O | N(CH$_3$)$_2$ | 196–198 | Butanol |
| 56 | NH—C$_6$H$_4$—CF$_3$ (m) | O | N(CH$_3$)$_2$ | 160–161 | Ethyl acetate/ligroin |
| 57 | NH—C$_6$H$_4$—OCH$_3$ (p) | O | N(CH$_3$)$_2$ | 170–172 | Butanol |

Table 3-continued

| Example No. | X | Y | Z | Melting point [° C] | Substance re-crystallised from |
|---|---|---|---|---|---|
| 58 | NH—⟨⟩—OCH₃, Cl | O | N(CH₃)₂ | 95–97 | Ethyl acetate/ligroin |
| 59 | NH—⟨⟩—C(O)—OC₂H₅ | O | N(CH₃)₂ | 173–174 | Ethanol |
| 60 | O—CH(CH₃)₂ | O | N(pyrrolidinyl) | 64–66 | Petroleum ether |
| 61 | —N(CH₃)(C₆H₅) | O | N(CH₃)₂ | 128–130 | Ligroin |
| 62 | —N(pyrrolidinyl) | O | N(CH₃)₂ | 118–120 | Toluene |
| 63 | —NH—⟨⟩—C(O)—N(CH₃)₂ | O | N(CH₃)₂ | 216–218 | Glycol-monomethylether |

Example 32a

Preparation of 3-(N′,N′-dimethylureido)-phenylacetic acid dimethylamide

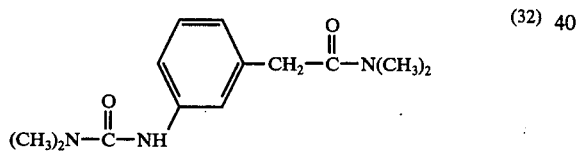

(32)

Process (c)

15.1 g (0.1 mol) of 3-amino-phenylacetic acid were stirred with 12.9 g (0.1 mol) of quinoline in 100 ml of toluene for 30 minutes at room temperature. The mixture was then saturated with phosgene whilst cooling at 5° to 10° C and was thereafter gradually warmed to the boil whilst continuing to introduce phosgene. At the boil, phosgene was passed in for a further hour. The mixture was allowed to cool somewhat and the toluene solution was separated from the heavier oil layer and distilled under reduced pressure. 12 g of 3-isocyanato-phenylacetic acid chloride distilled over at boiling point 0.06: 116° C ($n_D^{20}$: 1.5853). The product was added dropwise to a mixture of 8.5 g of dimethylamine (as an approximate 45% strength aqueous solution) and 100 ml of acetone at 10° to 15° C, whilst stirring vigorously. The mixture was stirred for a further hour at room temperature and was then diluted with 250 ml of water. The crystals which had separated out were filtered off and pressed out on clay. 12.5 g (83% of theory) of 3-(N′,N′-dimethylureido)-phenylacetic acid dimethylamide of melting point 80°–81° C were obtained.

Example 41a 3-(N′, N′-dimethylureido)-phenylacetic acid anilide

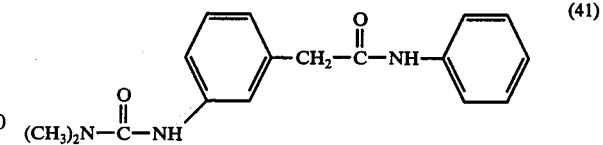

(41)

Process (d)

22.6 g (0.1 mol) of 3-amino-phenylacetic acid anilide were introduced in portions into 200 ml of toluene, saturated with phosgene, at room temperature. The mixture was gradually warmed to the boil in a slight stream of phosgene, until a practically clear solution had been produced. The toluene solution, containing 3-isocyanato-phenylacetic acid anilide, was decanted from small amounts of smeary constituents and excess gaseous dimethylamine was passed into this solution whilst cooling at 15° to 20° C. After stirring for one hour, the precipitate produced was filtered off, washed with water, recrystallized from ethanol and dried. 25 g (85.6% of theory) of 3-(N′,N′-dimethylureido)-phenylacetic acid anilide of melting point 158°–160° C were obtained.

Example 64

Preparation of
3-(methoxy-thiocarbamoyl)-phenyl-acetic acid anilide

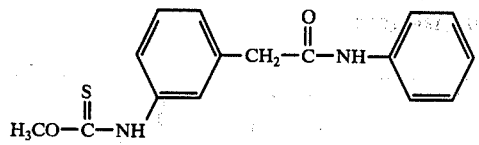

13.4 g (0.05 mol) of 3-isothiocyanato-phenylacetic acid anilide were dissolved in 100 ml of methanol. A solution of 1.15 g sodium in methanol was added dropwise at room temperature and the resulting mixture was stirred for a further 2 hours at a temperature of 40°–50° C. To isolate the product, the reaction mixture was poured into ice water and was acidified by adding diluted hydrochloric acid. The product which precipitated in crystalline form was filtered off and recrystallized from toluene. 9 g (60% of theory) of 3-(methoxy-thiocarbamoyl)-phenyl-acetic acid anilide of melting point 128°–130° C were obtained.

The 3-isothiocyanato-phenylacetic acid anilide of the formula:

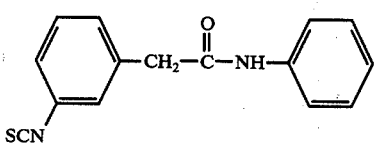

which was required as a starting material, was prepared as follows:

11.5 g (0.1 mol) of thiophosgen were added dropwise to a mixture of 22.6 g (0.1 mol) 3-amino-phenylacetic acid anilide, 20 ml of concentrated hydrochloric acid and 100 ml of water at a temperature of 10°–15° C. After stirring the reaction mixture for a further 2 hours, the product which precipitated in crystalline form was filtered off, washed with diluted hydrochloric acid and recrystallized from toluene. 26 g (97% of theory) of 3-isothiocyanato-phenylacetic acid anilide of melting point 109°–111° C were obtained.

Example 65

Preparation of
3-(isopropoxythio-carbamoyl)-phenylacetic acid anilide

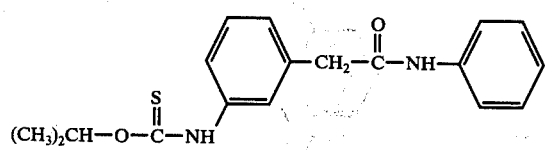

If 3-isothiocyanato-phenylacetic acid anilide was reacted with isopropanol in the way described in Example 64, 3-(isopropoxythio-carbamoyl)-phenylacetic acid anilide of melting point 157°–159° C (after recrystallization of the crude product from toluene) was obtained.

Example 66

Preparation of
3-(N,N'-dimethyl-thioureido)-phenylacetic acid anilide

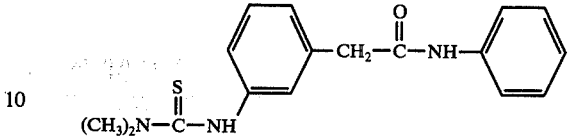

10 g of a 45% strength aqueous solution of dimethylamine were added dropwise to a solution of 13.4 (0.05 mol) of 3-isothiocyanato-phenylacetic acid anilide in 120 ml of acetone at room temperature. The reaction mixture was stirred for a further hour at a temperature of 50°–60° C and then was poured into ice water. The product which precipitated in crystalline form hereupon was filtered off and recrystallized from toluene. 13 g (83% of theory) of 3-(N,N'-dimethyl-thioureido)-phenylacetic acid anilide of melting point 163°–165° C were obtained.

The compounds of the formula (II) required as starting materials for the synthesis of the compounds of the formula (I), according to the invention, were prepared as follows: Example I

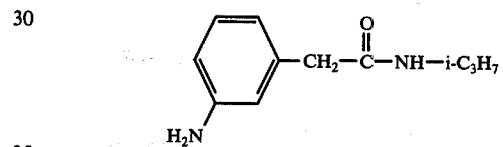

22.2 g (0.1 mol) of 3-nitrophenyl-acetic acid isopropylamide were dissolved in 150 ml of ethanol and hydrogenated under a hydrogen pressure of 40-50 atmospheres in the presence of Raney nickel at 50°–60° C. When the reaction had finished, the catalyst was filtered off, the filtrate was concentrated by evaporation under reduced pressure and the residue which remained was recrystallized from petroleum ether. 17.5 g (91% of theory) of 3-amino-phenylacetic acid isopropyl-amide of melting point 93°–95° C were obtained.

The compounds listed in Table 4 which follows were prepared analogously:

Table 4

| Example No. | X | Melting point [° C] |
|---|---|---|
| II | NH—CH$_3$ | 44–46 |
| III | NH—C$_2$H$_5$ | not crystalline |
| IV | NH-n-C$_3$H$_7$ | not crystalline |
| V | NH-n-C$_4$H$_9$ | not crystalline |
| VI | NH—CH$_2$—CH(CH$_3$)$_2$ | 38–40 |
| VII | NH—CH(CH$_3$)(C$_2$H$_5$) | 49–51 |

Table 4-continued

Structure: 3-aminophenyl-CH₂-C(=O)-X

| Example No. | X | Melting point [° C] |
|---|---|---|
| VIII | NH-C(CH₃)₃ | 81-83 |
| IX | N(CH₃)₂ | not crystalline |
| X | N(C₂H₅)₂ | not crystalline |
| XI | NH-cyclohexyl | 110-112 |
| XII | NH-phenyl | 98-100 |
| XIII | NH-(2-methylphenyl) | 90-92 |
| XIV | NH-(4-methylphenyl) | 100-102 |
| XV | NH-(2-chlorophenyl) | 69-71 |
| XVI | NH-(4-chlorophenyl) | 144-146 |
| XVII | N-(2-methyl-tetrahydropyranyl) | 48-50 |
| XVIII | NH-CH₂-(tetrahydropyranyl) | 150-152 |
| XIX | OCH₃ | not crystalline |
| XX | O-CH(CH₃)₂ | not crystalline |

The 3-nitro-phenylacetic acid derivatives which were used for the synthesis of the compounds mentioned in Examples I-XIII were prepared as follows:

Example Ia

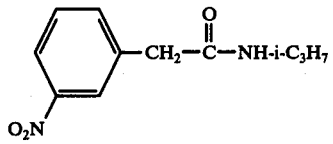

11.8 g (0.2 mol) of isopropylamine were added dropwise at 5° to 10° C to a solution of 20 g (0.1 mol) of 3-nitrophenylacetic acid chloride in 100 ml of acetone, whilst cooling. The mixture was stirred for a further hour at room temperature and was then poured into 250 ml of water. The precipitate which hereupon separated out was filtered off. After recrystallization from toluene, 18.8 g (85% of theory) of 3-nitro-phenylacetic acid isopropylamide of melting point 114°-116° were obtained.

The compounds in Table 5 which follows were prepared analogously:

Structure: 3-nitrophenyl-CH₂-C(=O)-X

| Example No. | X | Melting point [° C] |
|---|---|---|
| IIa | NH—CH₃ | 101-103 |
| IIIa | NH—C₂H₅ | 86-88 |
| IVa | NH-n-C₃H₇ | 107-109 |
| Va | NH-n-C₄H₉ | 71-73 |
| VIa | NH—CH₂—CH(CH₃)₂ | 72-73 |
| VIIa | NH—CH(C₂H₅)(CH₃) | 70-72 |
| VIIIa | NH—C(CH₃)₃ | 96-98 |
| IXa | N(CH₃)₂ | Oil |
| Xa | N(C₂H₅)₂ | Oil |
| XIa | NH-cyclohexyl | 157-158 |
| XIIa | NH-phenyl | 128-129 |
| XIIIa | NH-(2-methylphenyl) | 107-109 |
| XIVa | NH-(4-methylphenyl) | 128-130 |
| XVa | NH-(2-chlorophenyl) | 131-133 |
| XVIa | NH-(4-chlorophenyl) | 178-180 |
| XVIIa | NH—CH₂-(tetrahydropyranyl) | 93-95 |

-continued

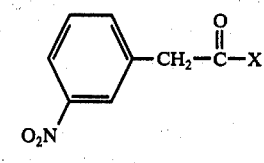

| Example No. | X | Melting point [° C] |
|---|---|---|
| XVIIIa | (tetrazole ring) | 108–110 |

The active compounds according to the invention influence plant growth and can therefore be used as defoliants, desiccants, herbage killers, germination inhibitors and, in particular, weedkillers. The term "herbicide" is used broadly to cover all these functions.

Weeds in the broadest sense are to be understood as all plants which grow in locations where they are not desired. Whether the compounds according to the invention act as total herbicides or selective herbicides depends essentially on the amount used.

The active compounds according to the invention can be used, for example, with the following plants:

Dicotyledon weeds of the genera: mustard (Sinapis), cress (Lepidium), bed straw (Galium), chickweed (Stellaria), camomile (Matricaria, mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), toothcup (Rotala), Lindernia (Linderia), deadnettle (Lamium), speedwell (Veronica), mallow (Abutilon), Emex, thornapple (Datura), violet (Viola), hempnettle (Galeopsis), poppy (Papaver) and knapweed (Centaurea).

Dicotyledon crops of the genera: cotton (Gossypium), soya bean (Glycine), beet (Beta), carrot (Daucus), bean (Phaseolus), pea (Pisum), potato (Solanum), flax (Linum), morning glory (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cuburbita).

Monocotyledon weeds of the genera: barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), Johnson grass (Sorghum), quackgrass (Agropyron), Bermuda grass (Cynodon)Monocharia, Fimbristylis, arrowhead (Sagittaria), spikerush (Eleocharis), bulrush (Scirpus), Paspalum, Ischaemum, gooseweed (Sphenoclea), crowfoot grass (Dactyloctenium), redtop (Agrostis), meadow foxtail (Alopecurus) and silky bent-grass (Apera).

Monocotyledon cultures of the genera: rice (Oryza), maize (Zea), wheat (Triticum), barley (Hordeum), oats (Avena), rye (Secale), Sorghum (Sorghum), millet (Panicum), sugar cane (Saccharum), pineapple (Ananas), asparagus (Asparagus) and onion (Allium).

The use of the active compounds according to the invention is in no way restricted to these genera but extends to other plants.

The compounds can be used, depending on the concentration, for total combating of weeds, for example on industrial installations, rail track systems and paths and areas with or without growing trees. Equally, the compounds can be employed for combating weeds in perennial cultures, for example in forestry or in growing ornamental trees, fruit, vines, citrus fruit, nuts, bananas, coffee, tea, rubber, oil palms, cocoa, soft fruit and hops, and for the selective combating of weeds in annual crops.

The active compounds according to the invention can be used as such, or as their formulations, also mixed with known herbicides, for combating weeds, it being possible to use finished formulations or to employ tank mixing.

The compounds according to the invention are suitable for the selective combating of weeds in cereals including maize, beans, soya beans, and cotton.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foamforming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, e.g. aerosol propellants, such as halogenated hydrocarbons, e.g. dichlorodifluoromethane or trichlorofluoromethane.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin, sulphite waste liquors and methyl cellulose.

The active compounds according to the invention can be used as a mixture with other active compounds, such as fungicides, insecticides and acaricides.

The formulations in general contain from 0.1 to 95 percent by weight of active compound, preferably 0.5 to 90.

The active compounds can be used as such or in the form of their formulations or as the use forms prepared therefrom, such as ready-to-use solutions, emulsions, foams, suspensions, powders, pastes and granules. They may be applied in the customary manner, for example by spraying, atomizing, dusting, scattering and watering.

They can be used both in accordance with the post-emergence process and in accordance with the pre-emergence process; when the active compounds are used as total herbicides, they are preferably applied after emergence of the plants whilst when they are used for the selective combating of weeds they are preferably applied before emergence.

The amount of active compound employed can vary within substantial ranges. It depends essentially on the nature of the desired effect. In general, the amounts applied to an area of agriculture are from 0.1 to 25 kg/ha, preferbly 0.25 to 10 kg/ha.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or a habitat thereof a compound according to the invention alone or in the form of a composition containing as active ingredient a compound according to the invention in admixture with a diluent or carrier.

The invention also provides crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, their preparation and their good herbicidal activity can be seen from the Examples which follow. In test Examples A and B, the compounds are numbered in accordance with the corresponding preparative Examples.

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denote:

0% = no action (like untreated control)
100% = total destruction

The active compounds, the amounts applied and the results can be seen from the table which follows:

Table A

| Pre-emergence test | | | | | | | | | | | |
|---|---|---|---|---|---|---|---|---|---|---|---|
| Compound | Amount of active compound used, kg/ha | Echino-chloa | Cheno-po-dium | Sina-pis | Stel-aria | Ga-lin-soga | Ma-tri-caria | Oats | Cotton | Wheat | Maize |
| (known) | 5 | 20 | 0 | 60 | 20 | 60 | 60 | 80 | 20 | 40 | 0 |
|  | 2.5 | 0 | 0 | 60 | 0 | 60 | 40 | 80 | 20 | 40 | 0 |
| (39) | 5 | 80 | 100 | 100 | 100 | 100 | 100 | 40 | 20 | 20 | 60 |
|  | 2.5 | 70 | 100 | 100 | 90 | 100 | 100 | 20 | 0 | 0 | 60 |
| (41) | 5 | 80 | 100 | 100 | 100 | 100 | 100 | 20 | 0 | 0 | 20 |
|  | 2.5 | 70 | 100 | 100 | 90 | 100 | 100 | 0 | 0 | 0 | 0 |

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5 – 15 cm were sprayed with the preparation of the active compound in such a way as to apply the amounts of active compound per unit area which are indicated in the table. The concentration of the spray liquor was so chosen that the amounts of active compound shown in the table were applied in 2,000 liters of water/ha. After three weeks, the degree of damage to the plants was rated in % damage in comparison to the development of the untreated control. The figures denote:

0% = no action (like untreated control)
100% = total destruction

The active compounds, the amounts applied and the results can be seen from the table which follows:

Table B

| Active compound | Amount of active compound used, kg/ha | Echi-no-chloa | Che-no-pod-ium | Sina-pis | Gal-in-soga | Stell-aria | Urti-ca | Ma-tri-caria | Cot-ton | Wheat | Beans |
|---|---|---|---|---|---|---|---|---|---|---|---|
| (known) [structure with NH-C(=O)-OCH₃, HN-C(=O)-O, CH₃] | 1<br>0.5 | 80<br>80 | 60<br>40 | 100<br>80 | 100<br>60 | 100<br>80 | 60<br>40 | 60<br>40 | 20<br>0 | 20<br>0 | 20<br>20 |
| (42) [(CH₃)₂N-C(=O)-HN-C₆H₄-CH₂-C(=O)-NH-C₆H₄-CH₃] | 1<br>0.5 | 100<br>80 | 100<br>90 | 100<br>100 | 100<br>90 | 100<br>80 | 100<br>100 | 60<br>50 | 20<br>0 | 20<br>0 | 0<br>0 |
| (18) [CH₃-HN-C(=O)-HN-C₆H₄-CH₂-C(=O)-HN-C₆H₅] | 1<br>0.5 | 100<br>90 | 100<br>90 | 100<br>100 | 100<br>80 | 100<br>80 | 100<br>100 | 90<br>80 | 20<br>0 | 40<br>20 | 20<br>0 |
| (41) [(CH₃)₂N-C(=O)-HN-C₆H₄-CH₂-C(=O)-NH-C₆H₅] | 1<br>0.5 | 100<br>100 | 100<br>100 | 100<br>100 | 100<br>100 | 100<br>100 | 100<br>100 | 100<br>100 | 20<br>0 | 80<br>60 | 20<br>0 |
| (38) [(CH₃)₂N-C(=O)-HN-C₆H₄-CH₂-C(=O)-NH-CH₂-CH(CH₃)₂] | 1<br>0.5 | 100<br>90 | 100<br>80 | 100<br>100 | 100<br>90 | 90<br>80 | 100<br>80 | 100<br>90 | 0<br>0 | 20<br>0 | 60<br>40 |
| (43) [(CH₃)₂N-C(=O)-HN-C₆H₄-CH₂-C(=O)-NH-C₆H₄-CH₃] | 1<br>0.5 | 100<br>100 | 100<br>100 | 100<br>100 | 100<br>100 | 100<br>90 | 100<br>90 | 100<br>100 | 20<br>0 | 20<br>0 | 80<br>60 |
| (28) [(CH₃)₂N-C(=O)-NH-C₆H₄-CH₂-C(=O)-NH-CH(C₂H₅)(CH₃)] | 1<br>0.5 | 100<br>80 | 100<br>80 | 100<br>100 | 100<br>100 | 100<br>80 | 100<br>100 | 80<br>60 | 20<br>0 | 20<br>0 | 60<br>60 |
| (44) [(CH₃)₂N-C(=O)-NH-C₆H₄-CH₂-C(=O)-NH-C₆H₄-Cl] | 1<br>0.5 | 100<br>100 | 100<br>100 | 100<br>100 | 100<br>100 | 100<br>100 | 100<br>100 | 100<br>100 | 20<br>0 | 40<br>20 | 40<br>20 |

It will be appreciated that the instant specification and examples are set forth by way of illustration and not limitation, and that various modifications and changes may be made without departing from the spirit and scope of the present invention.

What is claimed is:

1. 3-Amino-phenylacetic acid compound of the formula:

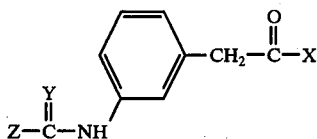
(I)

in which

X represents the group

in which

R¹ is hydrogen, alkyl of from 1 to 4 carbon atoms or alkenyl of from 2 to 4 carbon atoms, and R² is alkyl of from 1 to 15 carbon atoms, alkenyl of from 3 to 12 carbon atoms or alkynyl of from 3 to 12 carbon atoms, each of these alkyl, alkenyl and alkynyl radicals being optionally substituted by halogen, cyano, carboxylic acid ester groups, carboxylic acid amide groups, alkoxy, aryloxy, alkylmercapto, arylmercapto, alkylsulphonyl, or arylsulphonyl, or by aryl optionally substituted by halogen, alkyl, haloalkyl, alkoxy, alkylmercapto or nitro, or by optionally substituted cycloalkyl of from 3 to 6 carbon atoms where the substituent is $C_{1-3}$ alkyl group, or R² is cycloalkyl of from 3 to 8 carbon atoms in the ring, optionally substituted by alkyl, halogen or alkoxy, or R² is aryl of from 6 to 10 carbon atoms optionally monosubstituted or polysubstituted by halogen, nitro, cyano, carboxylic acid ester or carboxylic acid amide, alkyl of from 1 to 6 carbon atoms, cycloalkyl of from 5 or 6 carbon atoms, alkoxy, haloalkoxy, aryloxy, alkylmercapto, arylmercapto, alkylsulphonyl, arylsulphonyl, haloalkyl or thiocyano, Y is oxygen or sulphur, and Z represents the group

in which

R⁴ is hydrogen, alkyl of from 1 to 4 carbon atoms or alkenyl of from 2 to 4 carbon atoms, and R⁵ is alkyl of from 1 to 4 carbon atoms which is optionally substituted by halogen or alkoxy, alkenyl of from 2 to 4 carbon atoms, alkynyl of from 3 to 6 carbon atoms or optionally alkyl-substituted cycloalkyl of 5 to 6 carbon atoms.

2. 3-Amino-phenylacetic acid compound as claimed in claim 1 wherein R¹ is alkyl from 1 to 6 carbon atoms.

3. 3-Amino-phenylacetic acid compound as claimed in claim 1 wherein R¹ is substituted alkyl wherein the substituent is at least one of fluorine, chlorine, bromine, iodine, alkoxy of from 1 to 4 carbon atoms, and arylmercapto from 6 to 10 carbon atoms.

4. 3-Amino-phenylacetic acid compound as claimed in claim 1 wherein R¹ is hydrogen.

5. 3-Amino-phenylacetic acid compound as claimed in claim 1 wherein R¹ is alkyl of from 1 to 3 carbon atoms.

6. 3-Amino-phenylacetic acid compound as claimed in claim 1 wherein R¹ is alkenyl of from 2 to 4 carbon atoms.

7. 3-Amino-phenylacetic acid compound as claimed in claim 1 wherein R² is alkyl of from 1 to 12 carbon atoms.

8. 3-Amino-phenylacetic acid compound as claimed in claim 1 wherein R² is alkenyl or alkynyl of from 3 to 6 carbon atoms.

9. 3-Amino-phenylacetic acid compound as claimed in claim 1 wherein R² is alkyl, alkenyl or alkynyl of up to 6 carbon atoms substituted by at least one member of the group consisting of fluorine, chlorine, bromine, iodine; cyano; carbalkoxy of from 1 to 4 carbon atoms in the alkyl moiety; alkylaminocarbonyl or dialkylaminocarbonyl of from 1 to 4 carbon atoms in each alkyl moiety; alkoxy and alkylmercapto of from 1 to 4 carbon atoms; aryloxy of from 6 to 10 carbon atoms, arylmercapto of from 6 to 10 carbon atoms and arylsulfonyl of from 6 to 10 carbon atoms, wherein such aryl moieties may be substituted by at least one member of the group consisting of halogen, alkyl of from 1 to 3 carbon atoms, haloalkyl of from 3 carbon atoms and 1 to 5 halogen atoms, alkoxy of from 1 to 3 carbon atoms, alkylmercapto of from 1 to 3 carbon atoms, nitro; cycloalkyl of 5 to 6 carbon atoms in the ring, optionally substituted by alkyl of from 1 to 3 carbon atoms.

10. 3-Amino-phenylacetic acid compound as claimed in claim 1 wherein R² is cycloalkyl of 3 to 6 carbon atoms.

11. 3-Amino-phenylacetic acid compound as claimed in claim 1 wherein R² is cycloalkyl of from 3 to 6 carbon atoms substituted by at least one member of the group consisting of alkyl of from 1 to 3 carbon atoms, fluorine, chlorine, bromine, iodine, alkoxy of from 1 to 3 carbon atoms.

12. 3-Amino-phenylacetic acid compound as claimed in claim 1 wherein R² is aryl selected from phenyl and naphthyl.

13. 3-Amino-phenylacetic acid compound as claimed in claim 1 wherein R² is phenyl or naphthyl substituted by at least one of the following: fluorine, chlorine, bromine, iodine, nitro, cyano, thiocyano, carbalkoxy of from 1 to 4 carbon atoms in the alkyl moiety, alkylaminocarbonyl or dialkylaminocarbonyl of from 1 to 4 carbon atoms in each alkyl moeity, alkyl of from 1 to 4 carbon atoms, cyclohexyl, alkoxy of from 1 to 4 carbon atoms, haloalkoxy of from 1 to 4 carbon atoms and 1 to 5 halogen atoms, aryloxy of from 6 to 10 carbon atoms, alkylmercapto of from 1 to 4 carbon atoms, arylmercapto of from 6 to 10 carbon atoms, alkylsulfonyl of from 1 to 4 carbon atoms and arylsulfonyl of from 6 to 10 carbon atoms, haloalkyl of from 1to 4 carbon atoms and 1 to 5 halogen atoms, and thiocyano.

14. 3-Amino-phenylacetic acid compound as claimed in claim 1 wherein R⁴ is alkyl or alkenyl of up to 4 carbon atoms and R⁵ is alkyl optionally substituted by at least one member of halogen and alkoxy of from 1 to 3 carbon atoms, alkenyl or alkynyl of up to 6 carbon atoms or cycloalkyl optionally substituted by at least one of alkyl of from 1 to 3 carbon atoms.

15. 3-Aminophenylacetic acid compound as claimed in claim 1 designated 3-(N,N'-dimethylureido)phenyl acetic acid butyl amide.

16. 3-Aminophenylacetic acid compound as claimed in claim 1 designated 3-(N,N'-dimethylureido)phenyl acetic acid tert.-butyl amide.

17. 3-Aminophenylacetic acid compound as claimed in claim 1 designated 3-(N,N'-dimethylureido)phenyl-acetic acid anilide.

18. 3-Aminophenylacetic acid compound as claimed in claim 1 designated 3-(N,N'-dimethylureido)phenyl-acetic acid 3-methylanilide.

19. 3-Aminophenylacetic acid compound as claimed in claim 1 designated 3-(N,N'-dimethylureido)phenyl acetic acid 3-chloroanilide.

20. A herbicidal composition comprising in an agriculturally acceptable carrier an effective herbicidal amount of a 3-aminophenylacetic acid compound as claimed in claim 1.

21. Method of combating undesired vegetation which comprises applying to said vegetation or its habitat a herbicidally effective amount of a 3-aminophenylacetic acid compound of the formula

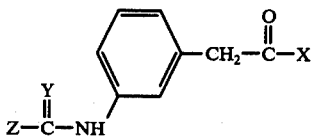

in which

X represents the group

in which $R^1$ is hydrogen, alkyl of from 1 to 4 carbon atoms or alkenyl of from 2 to 4 carbon atoms, and $R^2$ is alkyl of from 1 to 15 carbon atoms, alkenyl of from 3 to 12 carbon atoms or alkynyl of from 3 to 12 carbon atoms, each of these alkyl, alkenyl and alkynyl radicals being optionally substituted by halogen, cyano, carboxylic acid ester groups, carboxylic acid amide groups, alkoxy, aryloxy, alkylmercapto, arylmercapto, alkylsulphonyl, or arylsulphonyl, or by aryl optionally substituted by halogen, alkyl, haloalkyl, alkoxy, alkylmercapto or nitro, or by optionally substituted cycloalkyl of from 3 to 6 carbon atoms where the substituent is $C_{1-3}$ alkyl group or $R^2$ is cycloalkyl of from 3 to 8 carbon atoms in the ring, optionally substituted by alkyl, halogen or alkoxy, or $R^2$ is aryl of from 6 to 10 carbon atoms optionally monosubstituted or polysubstituted by halogen, nitro, cyano, carboxylic acid ester or carboxylic acid amide, alkyl of from 1 to 6 carbon atoms, cycloalkyl of from 5 or 6 carbon atoms, alkoxy, haloalkoxy, aryloxy, alkylmercapto, arylmercapto, alkylsulphonyl, arylsulphonyl, haloalkyl or thiocyano, Y is oxygen or sulphur, and Z represents the group

in which $R^4$ is hydrogen, alkyl of from 1 to 4 carbon atoms or alkenyl of from 2 to 4 carbon atoms, and $R^5$ is alkyl of from 1 to 4 carbon atoms which is optionally substituted by halogen or alkoxy, alkenyl of from 2 to 4 carbon atoms, alkynyl of from 3 to 6 carbon atoms or optionally alkyl-substituted cycloalkyl of 5 or 6 carbon atoms.

22. Method as claimed in claim 21 wherein said compound is at least one member of the group consisting of 3-(N,N'-dimethylureido)phenyl acetic acid isobutyl amide;

3-(N,N'-dimethylureido)phenyl acetic acid tert.-butyl amide;

3-(N,N'-dimethylureido)phenyl acetic acid 3-methylanilide; and 3-(N,N'-dimethylureido)phenyl acetic acid 3-chloroanilide.

* * * * *